United States Patent [19]

Courtney, Jr. et al.

[11] Patent Number: 4,631,194
[45] Date of Patent: Dec. 23, 1986

[54] ESTERS OF ALKYLTHIOALKANOIC ACIDS

[75] Inventors: Thomas F. Courtney, Jr., Keyport; Alan O. Pittet, Atlantic Highlands; Ranya Muralidhara, Fair Haven; Manfred H. Vock, Locust; Charles Wiener, Middletown, all of N.J.

[73] Assignee: International Flavors & Fragrances Inc., New York, N.Y.

[21] Appl. No.: 789,162

[22] Filed: Dec. 6, 1985

[51] Int. Cl.$^4$ ................ A23L 1/226; A23L 1/231; A23L 1/235
[52] U.S. Cl. .................................. 426/535; 560/152
[58] Field of Search .................... 426/535; 560/152

[56] References Cited

U.S. PATENT DOCUMENTS

| | | | |
|---|---|---|---|
| 3,870,800 | 3/1975 | Pittet et al. | 426/535 |
| 4,426,403 | 1/1984 | Cyronak et al. | 426/535 |
| 4,590,082 | 5/1986 | Pittet et al. | 426/535 |

FOREIGN PATENT DOCUMENTS 3307166  9/1983  Fed. Rep. of Germany .

OTHER PUBLICATIONS

Schultz et al., The Chemistry and Physiology of Flavors, 1967, Avi: Westport, Conn., pp. 450, 451, 452, 461.
Haagen-Smit et al., J. Am. Chem. Soc., vol. 67, Oct. 1945, pp. 1646-1652.

*Primary Examiner*—Joseph Golian
*Attorney, Agent, or Firm*—Arthur L. Liberman

[57] ABSTRACT

Described are the esters of alkylthioalkanoic acids defined according to the structure:

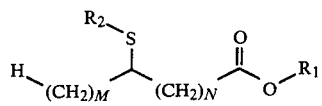

wherein $R_1$ represents $C_3$–$C_6$ alkenyl or $C_1$–$C_4$ alkyl; $R_2$ represents $C_3$ alkyl; $C_3$ hydroxyalkyl or $C_3$ alkenyl; N represents 0, 1 or 2 and M represents 0 or 1 and uses thereof in augmenting or enhancing the aroma or taste of foodstuffs.

12 Claims, 32 Drawing Figures

FIG. I
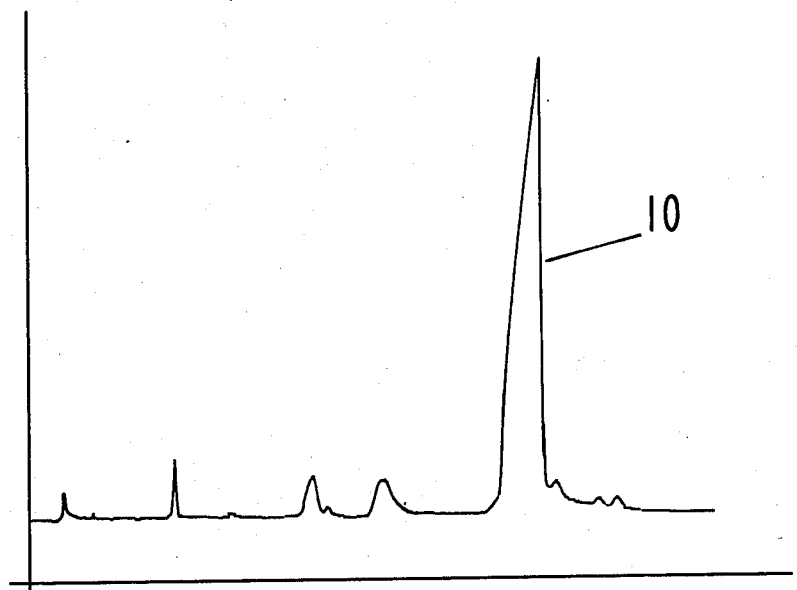
GLC PROFILE FOR FRACTION 5 OF EXAMPLE I.
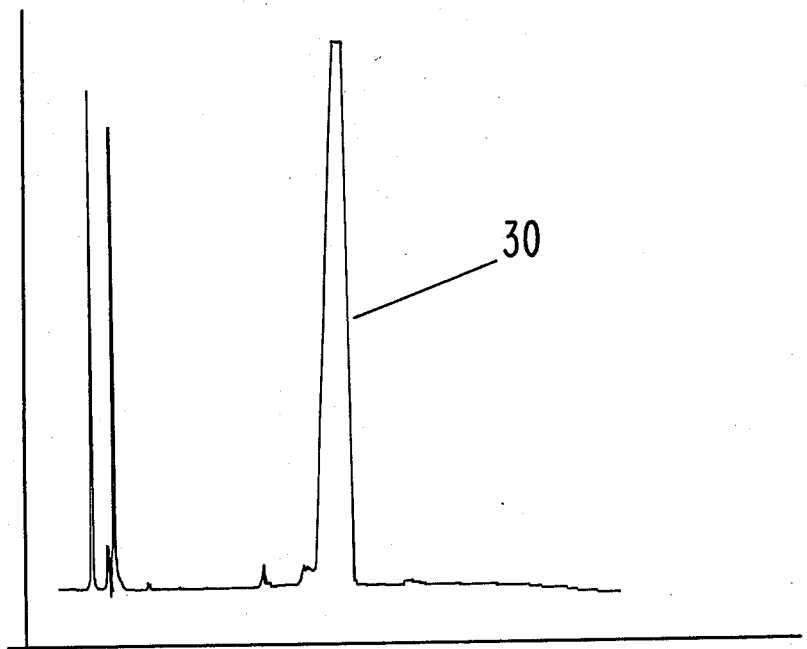
GLC PROFILE FOR EXAMPLE II. CRUDE
FIG. 3

NMR SPECTRUM FOR FRACTION 5 OF EXAMPLE I

FIG.3A
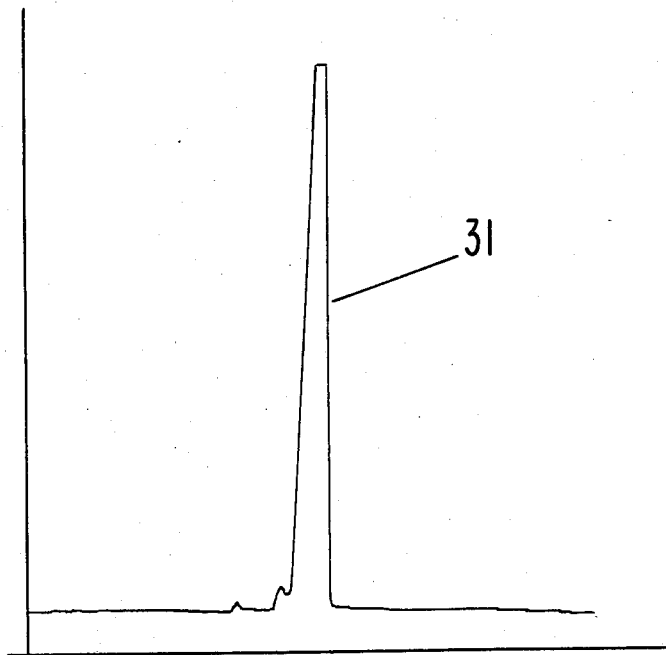
GLC PROFILE FOR FRACTION 5 OF EXAMPLE II.
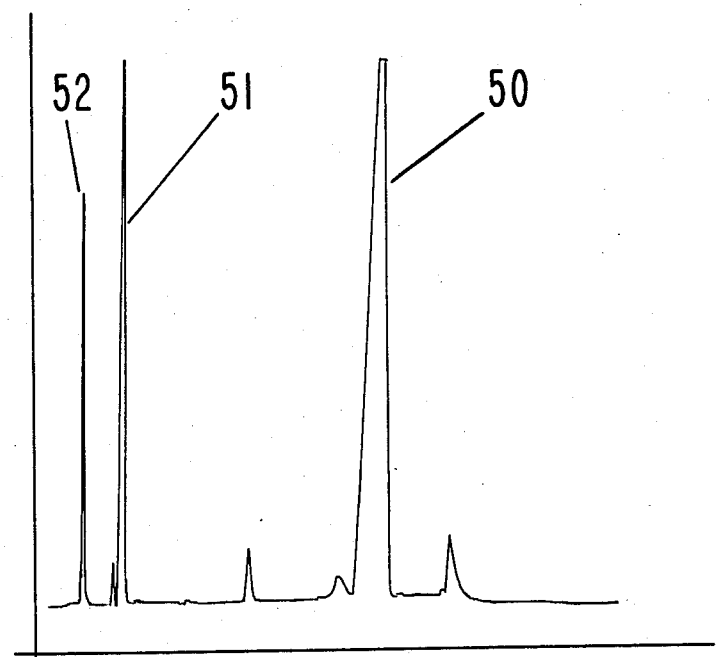
GLC PROFILE FOR EXAMPLE III. CRUDE
FIG.5

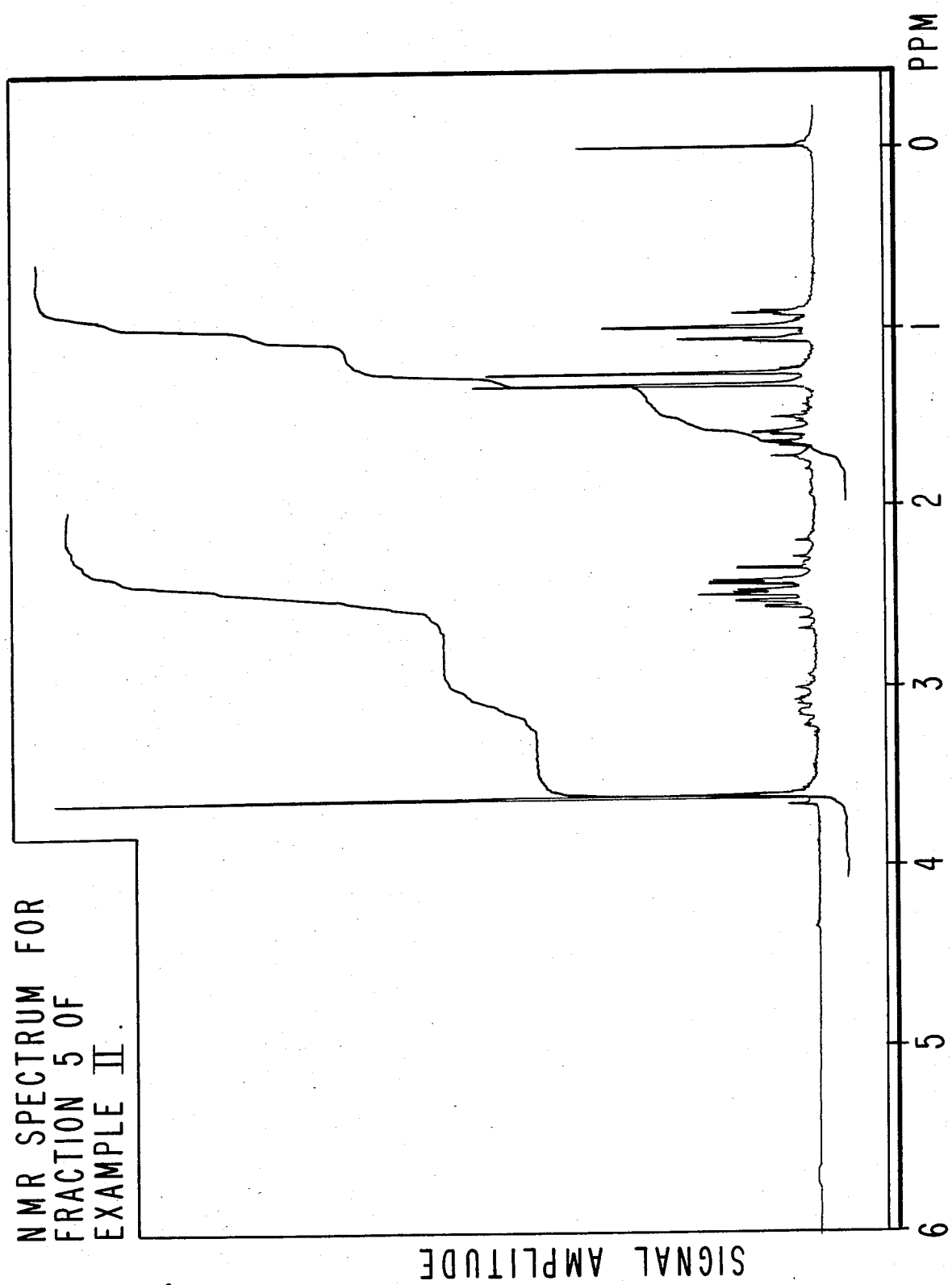
FIG. 4 NMR SPECTRUM FOR FRACTION 5 OF EXAMPLE II.

GLC PROFILE FOR FRACTION 6 OF EXAMPLE III.

GLC PROFILE FOR EXAMPLE IV. CRUDE.

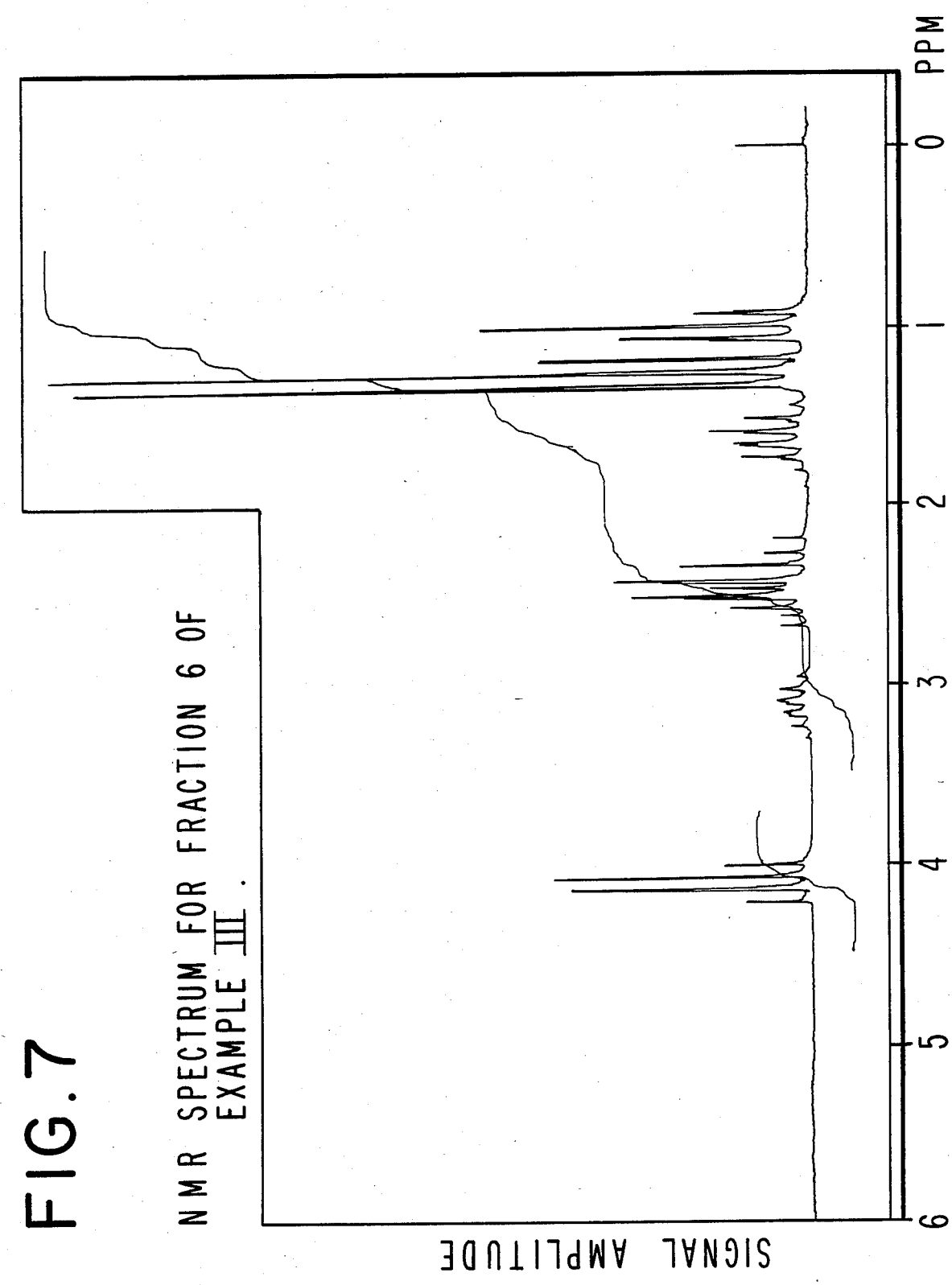
FIG. 7 NMR SPECTRUM FOR FRACTION 6 OF EXAMPLE III.

GLC PROFILE FOR FRACTION 6 OF EXAMPLE IV.

GLC PROFILE FOR EXAMPLE V. CRUDE

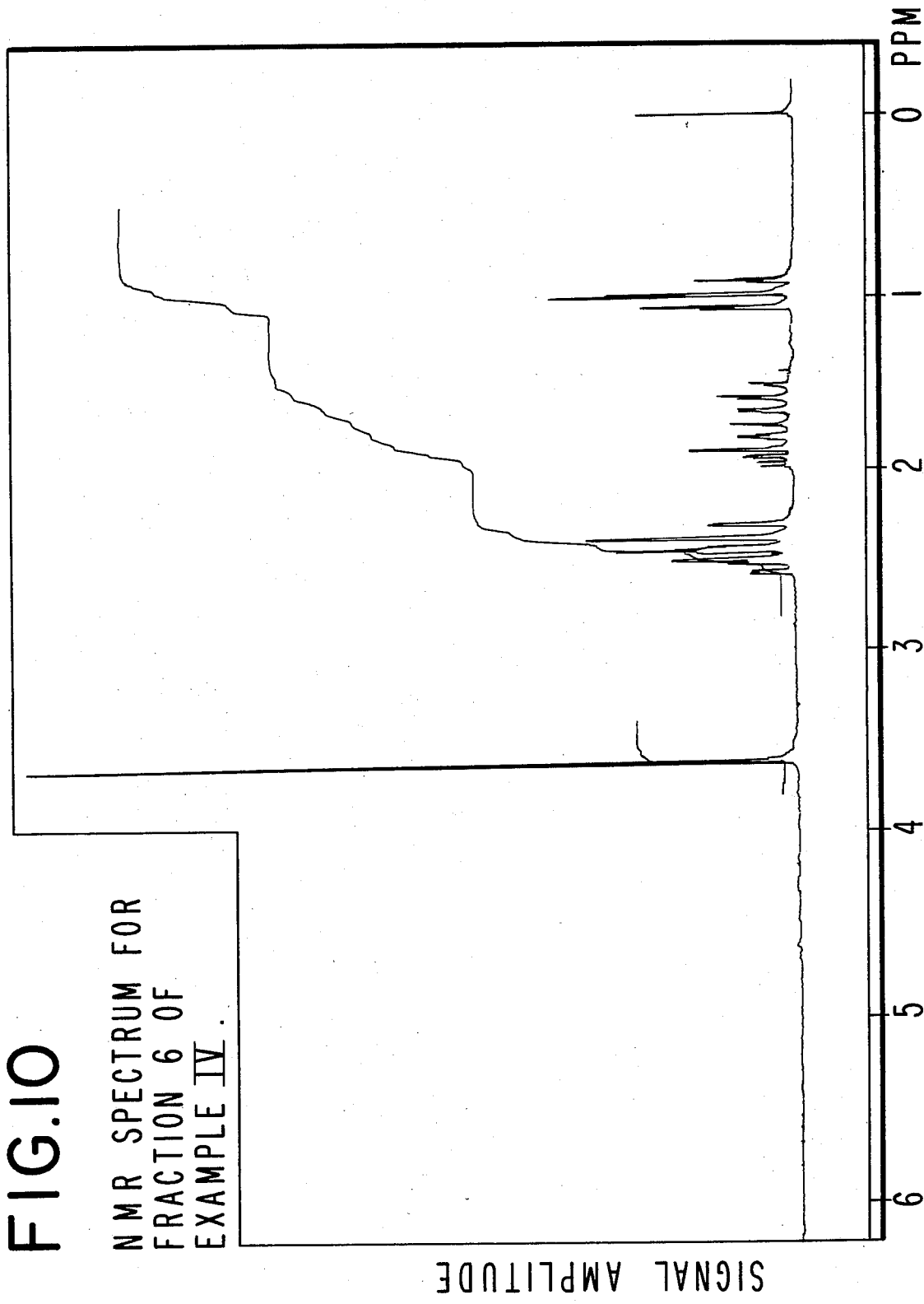
FIG.10 NMR SPECTRUM FOR FRACTION 6 OF EXAMPLE IV.

FIG.12
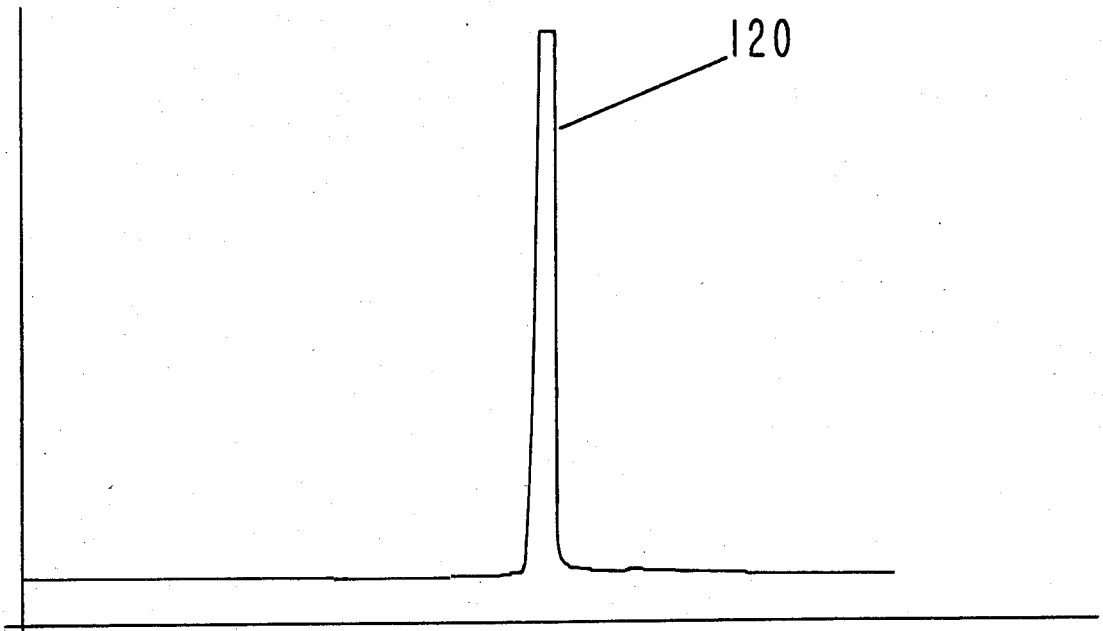
GLC PROFILE FOR FRACTION 10 OF EXAMPLE V.
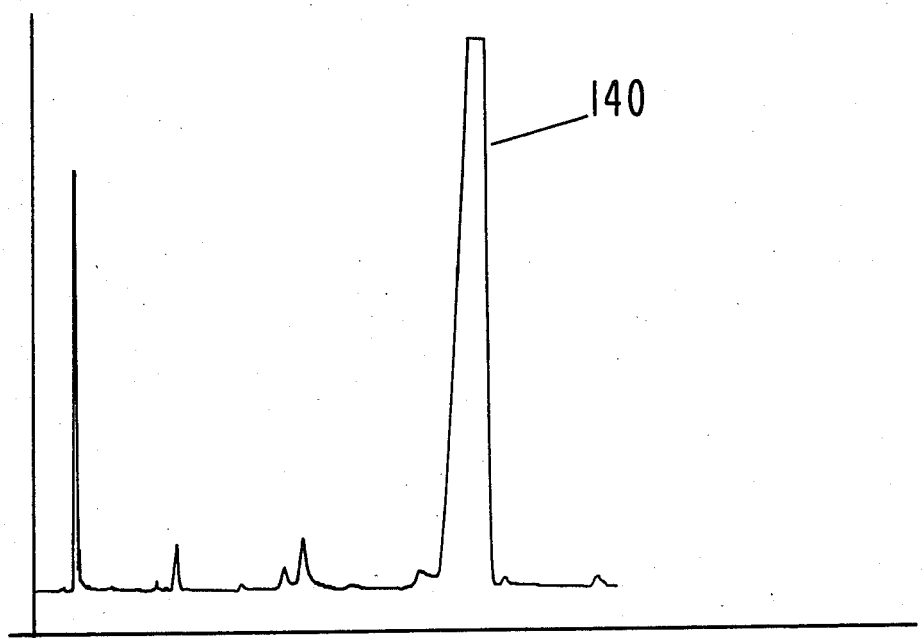
GLC PROFILE FOR EXAMPLE VI. CRUDE
FIG.14

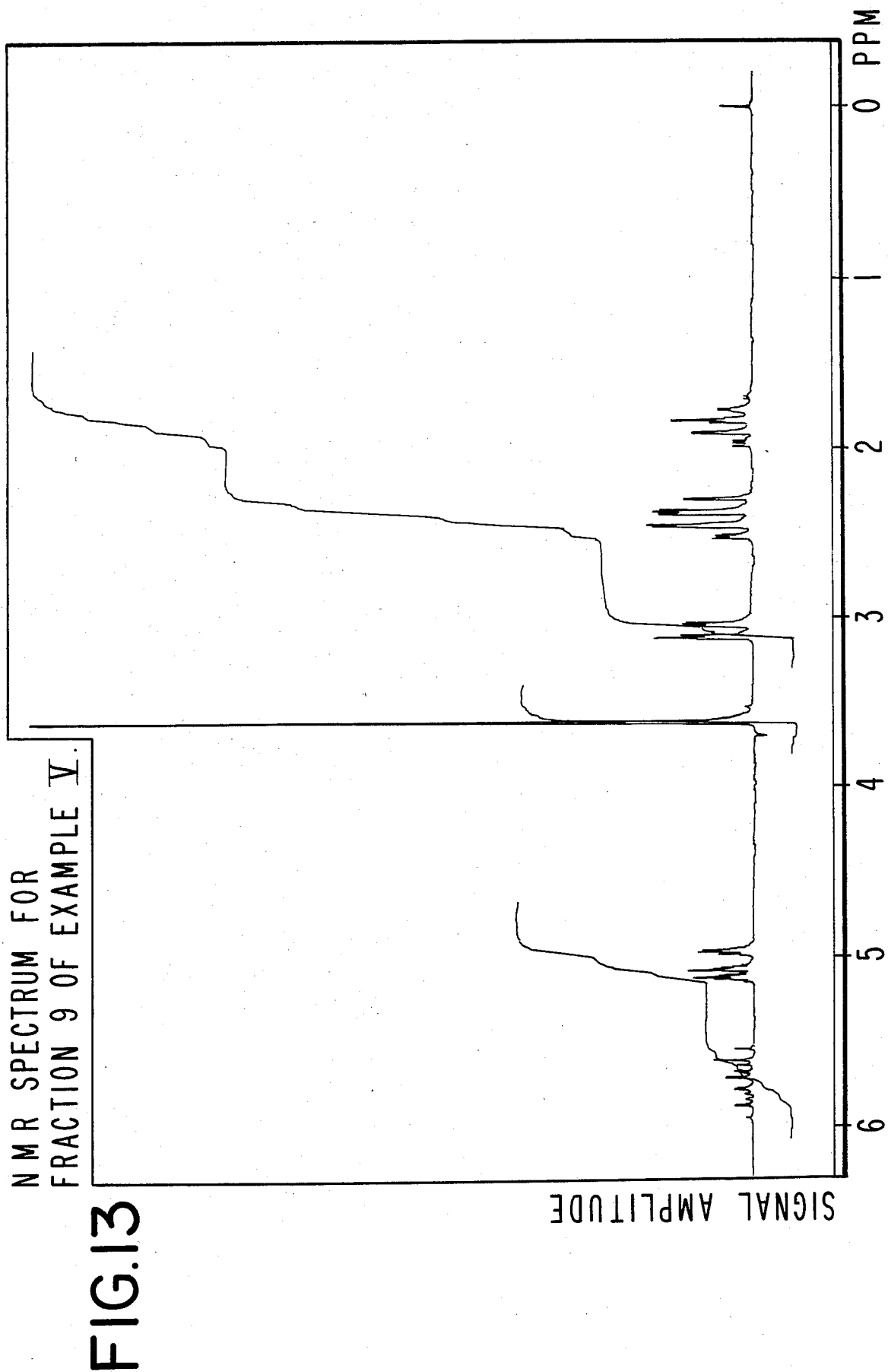

FIG.15
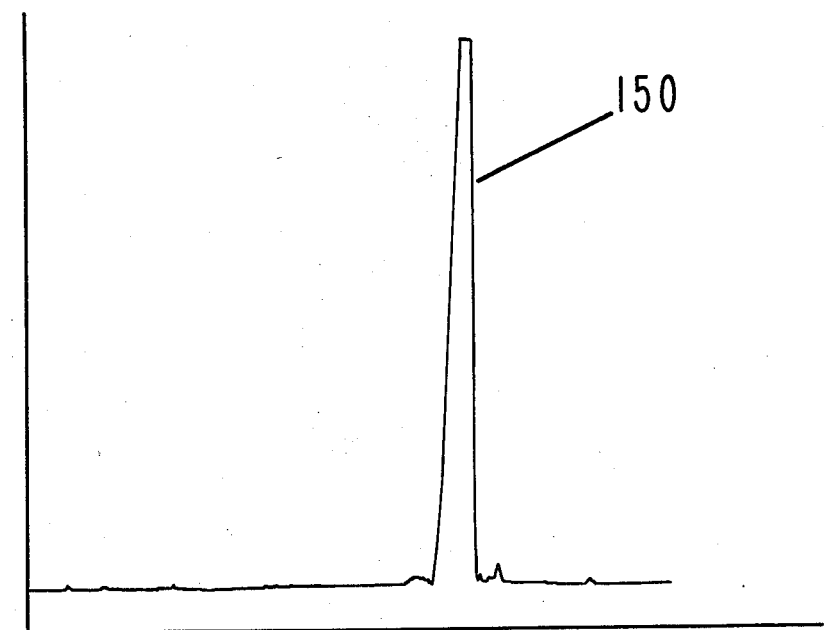
GLC PROFILE FOR EXAMPLE VI, FRACTION 4.
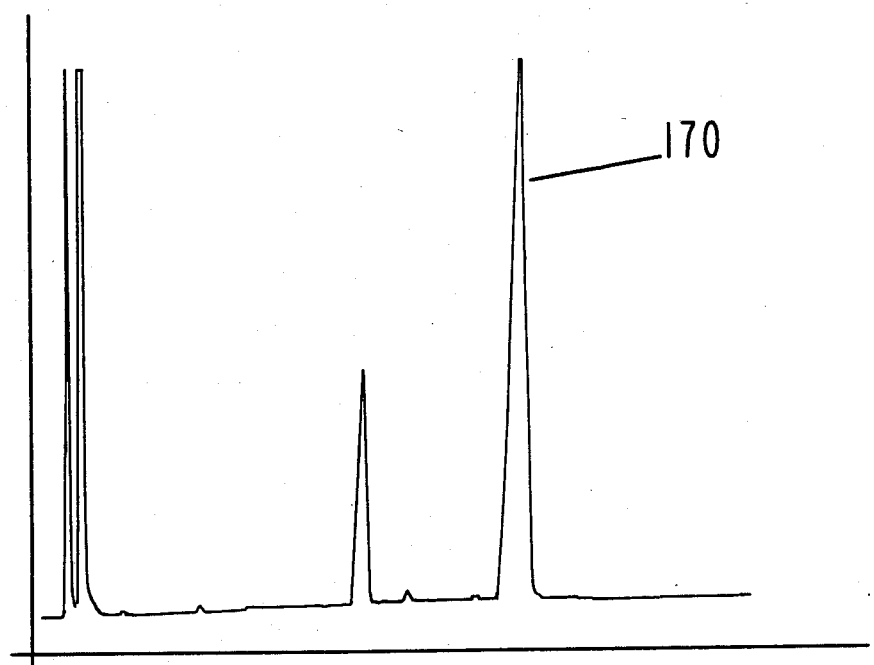
GLC PROFILE FOR EXAMPLE VII. CRUDE
FIG.17

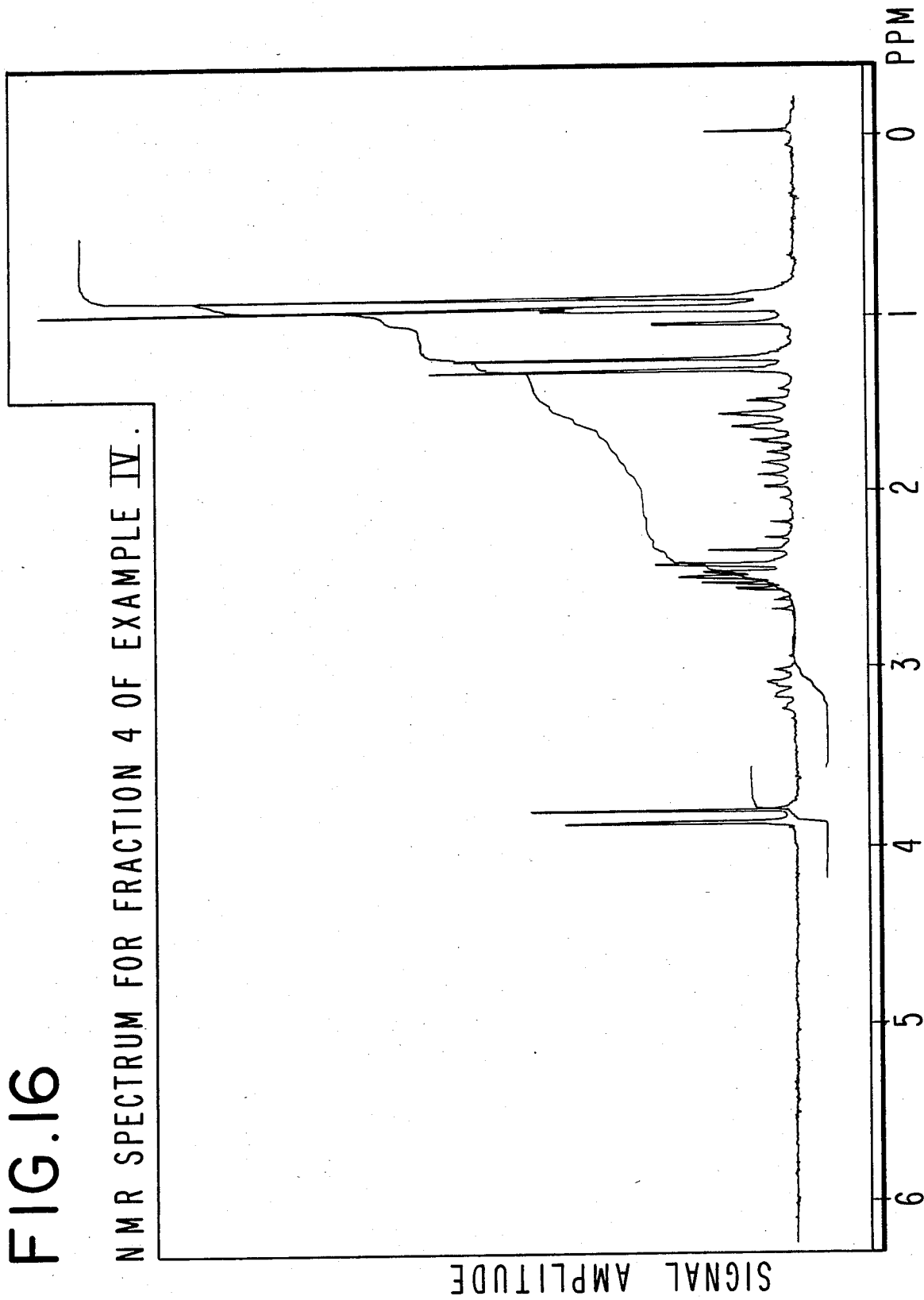
FIG. 16 NMR SPECTRUM FOR FRACTION 4 OF EXAMPLE IV.

GLC PROFILE FOR FRACTION 5 OF EXAMPLE VII.

GLC PROFILE FOR EXAMPLE VIII. CRUDE

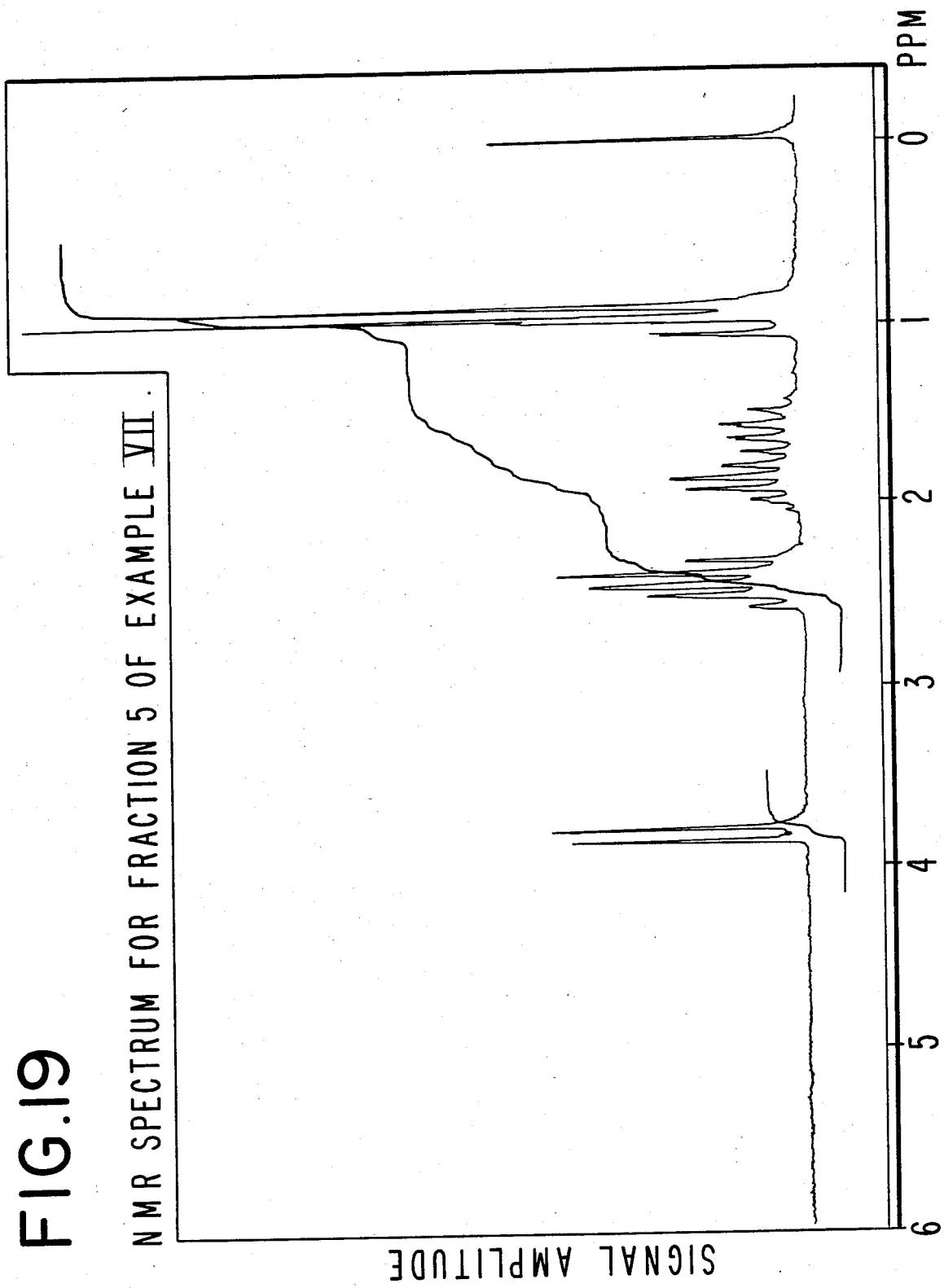
FIG.19 NMR SPECTRUM FOR FRACTION 5 OF EXAMPLE VII

GLC PROFILE FOR FRACTION 4 OF EXAMPLE VIII.

GLC PROFILE FOR EXAMPLE IX. CRUDE

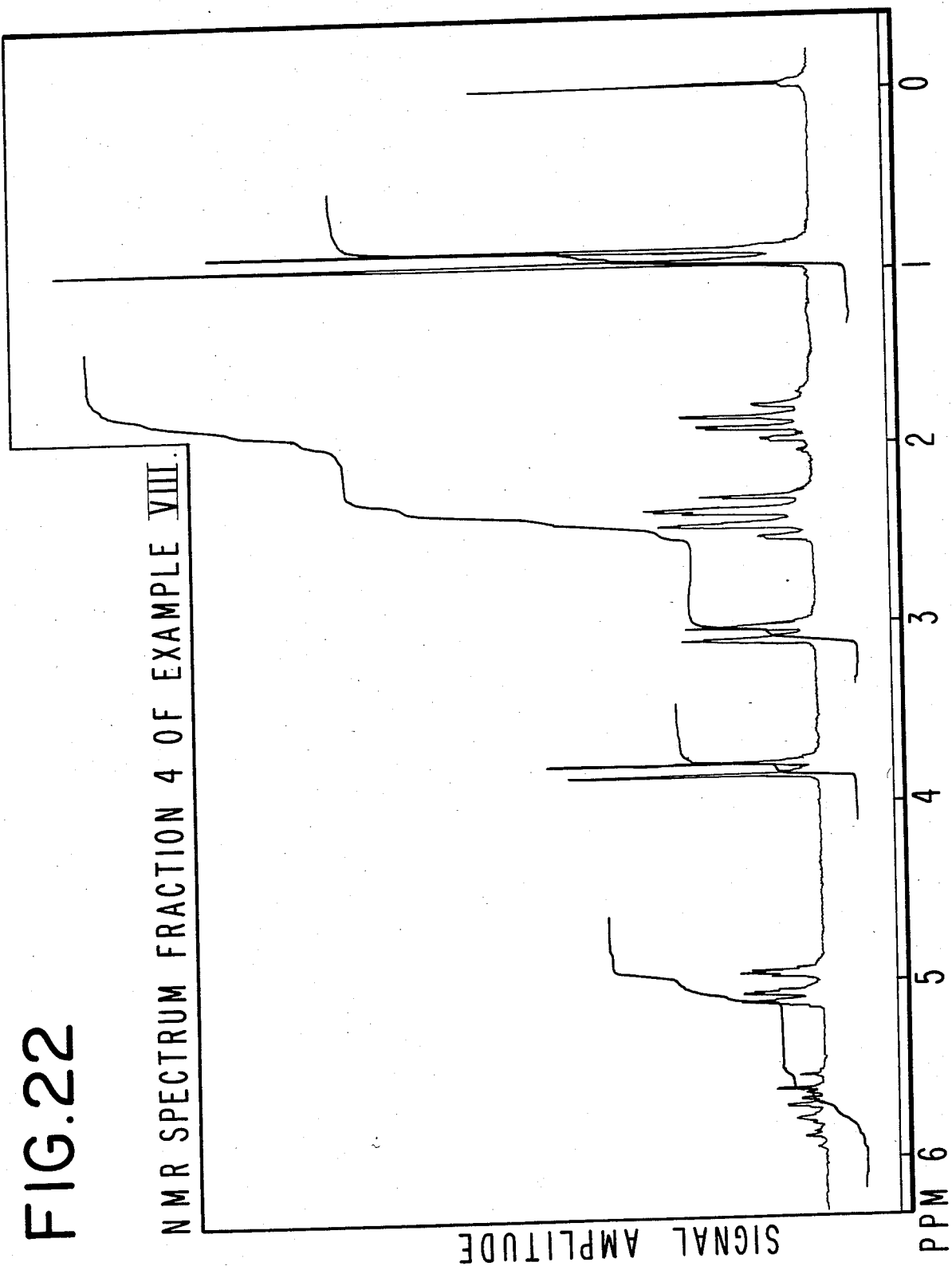
FIG. 22 NMR SPECTRUM FRACTION 4 OF EXAMPLE VIII.

FIG. 24
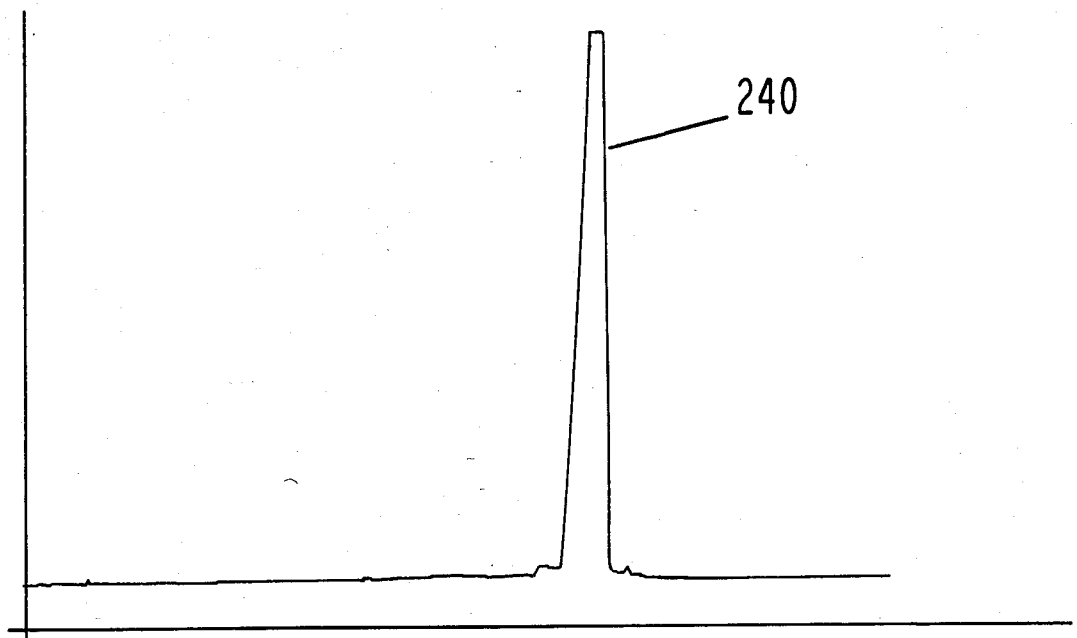
GLC PROFILE FOR FRACTION 5 OF EXAMPLE IX.
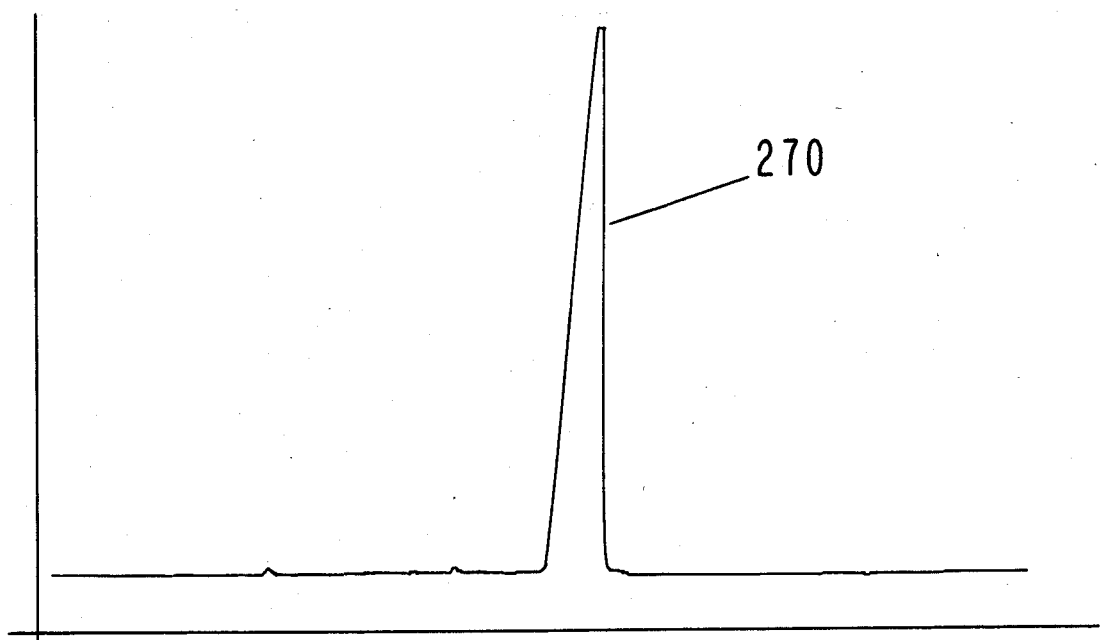
GLC PROFILE FOR FRACTION 4 OF EXAMPLE X.
FIG. 27

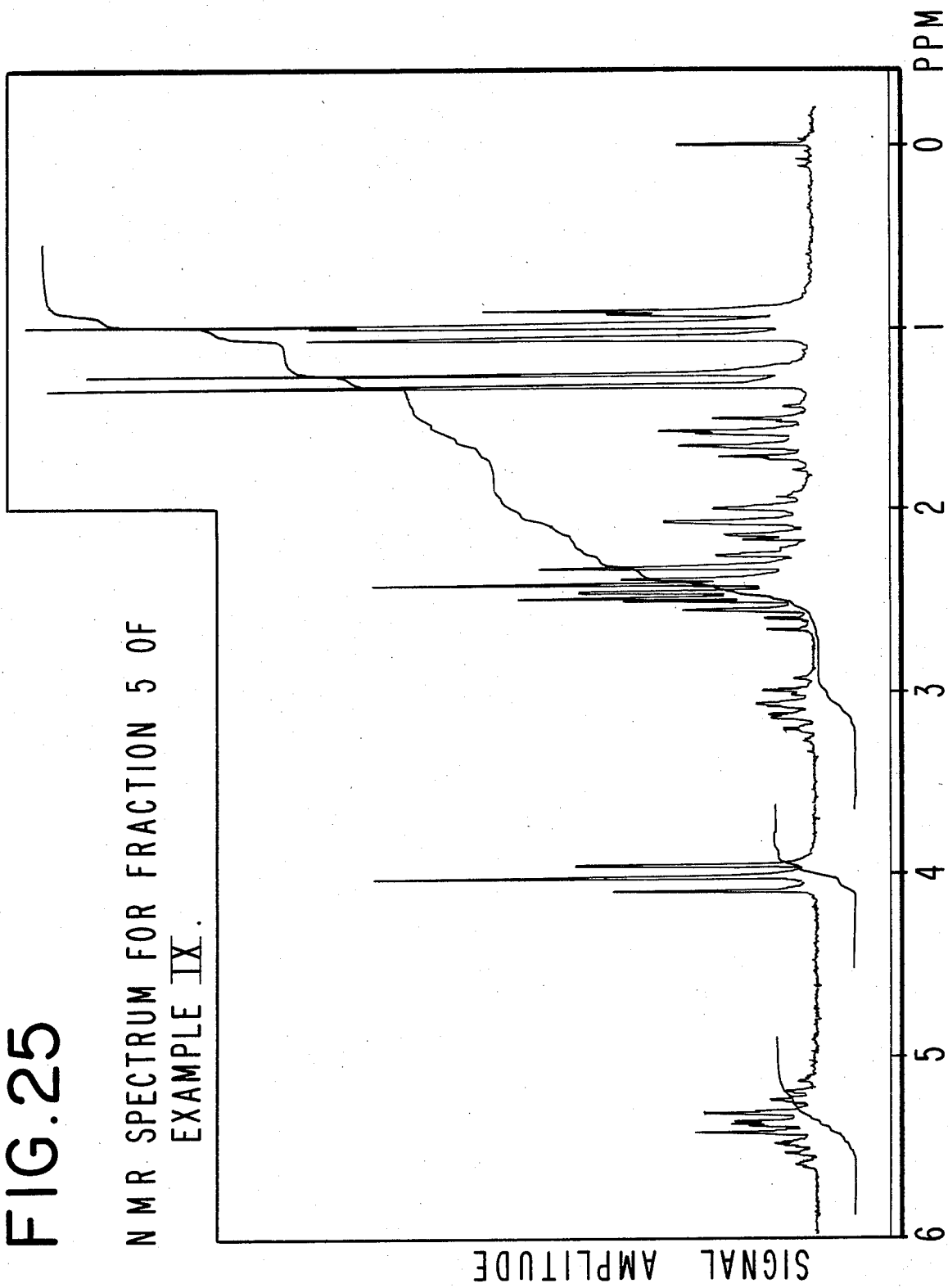
FIG. 25 NMR SPECTRUM FOR FRACTION 5 OF EXAMPLE IX.

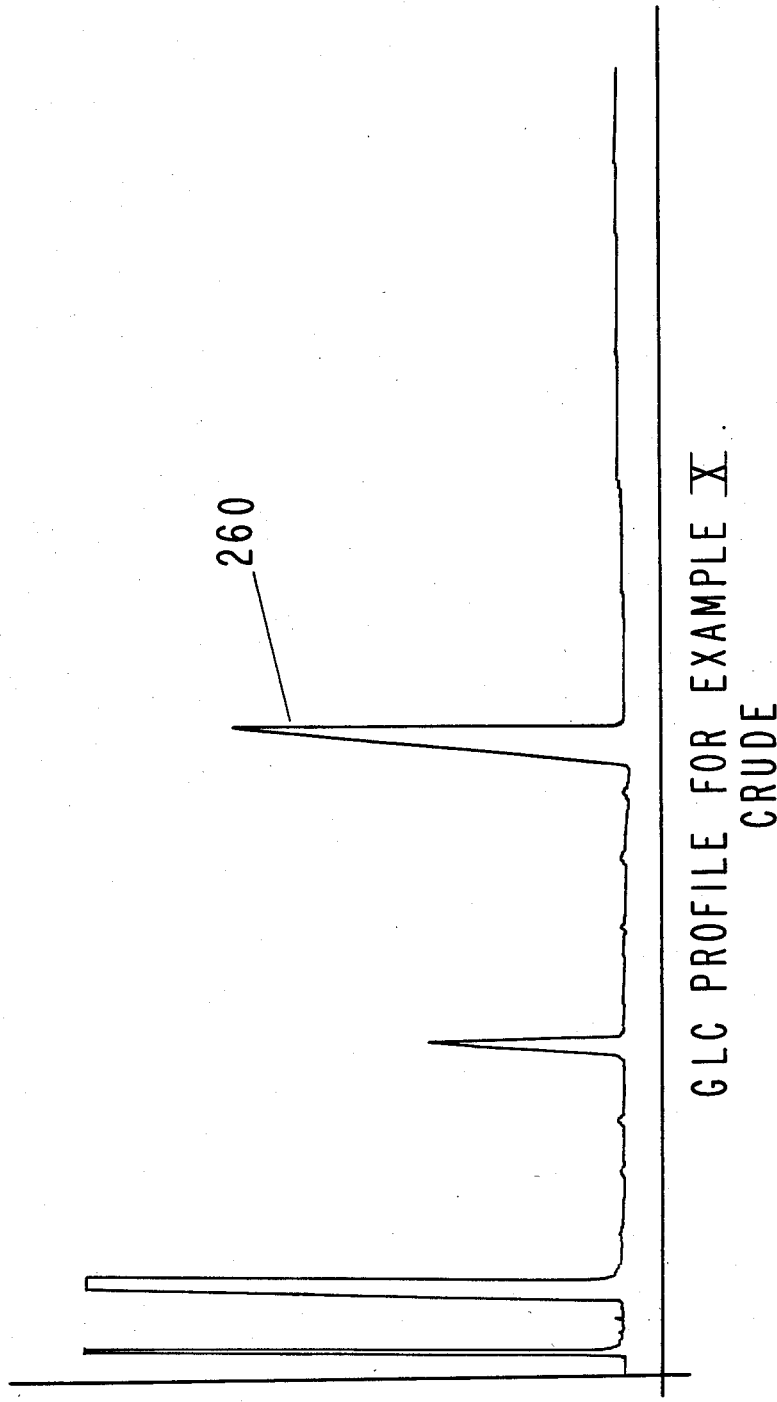

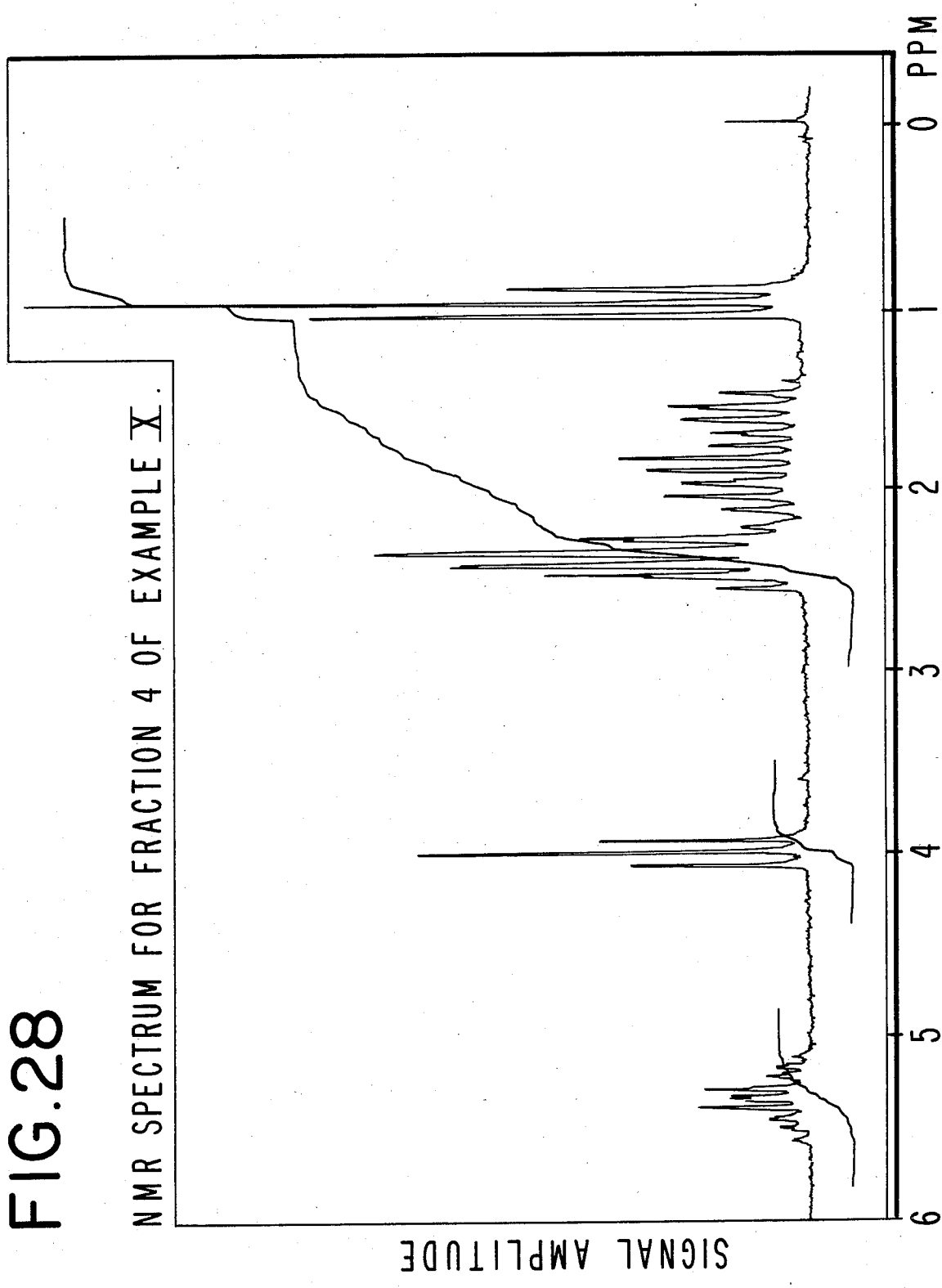
FIG. 28 NMR SPECTRUM FOR FRACTION 4 OF EXAMPLE X.

FIG.29
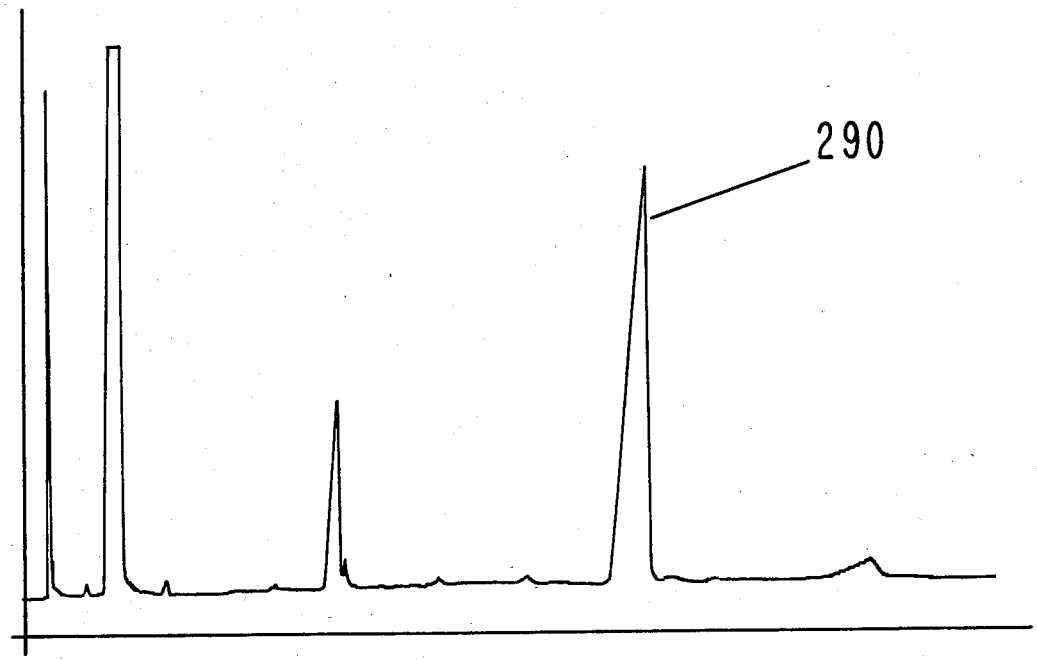
GLC PROFILE FOR EXAMPLE XI. CRUDE.
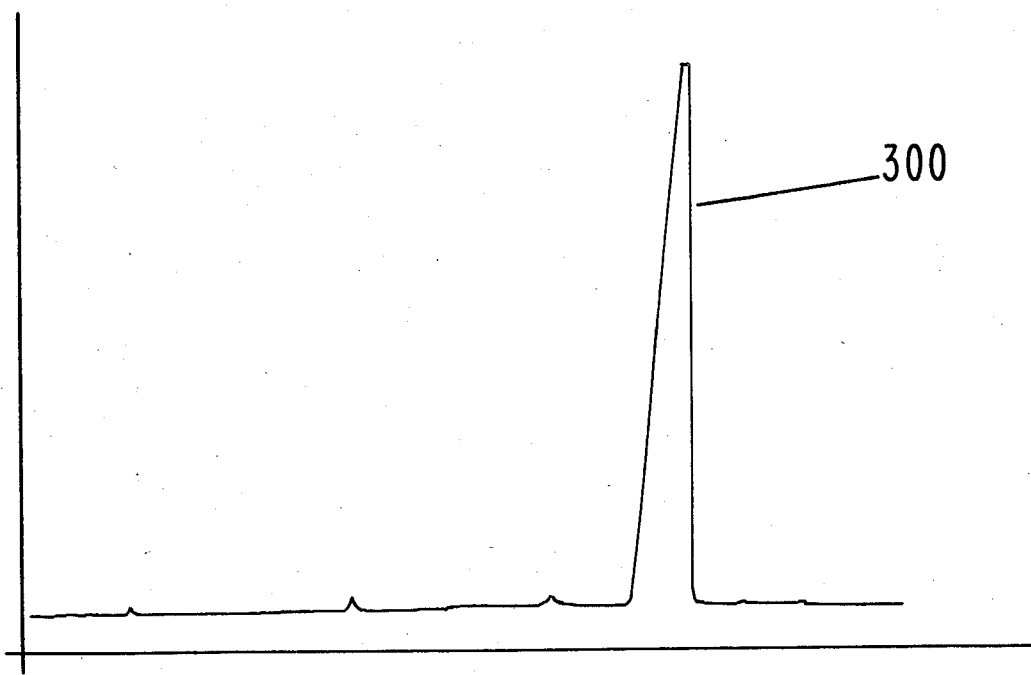
GLC PROFILE FOR FRACTION 5 OF EXAMPLE XI.
FIG.30

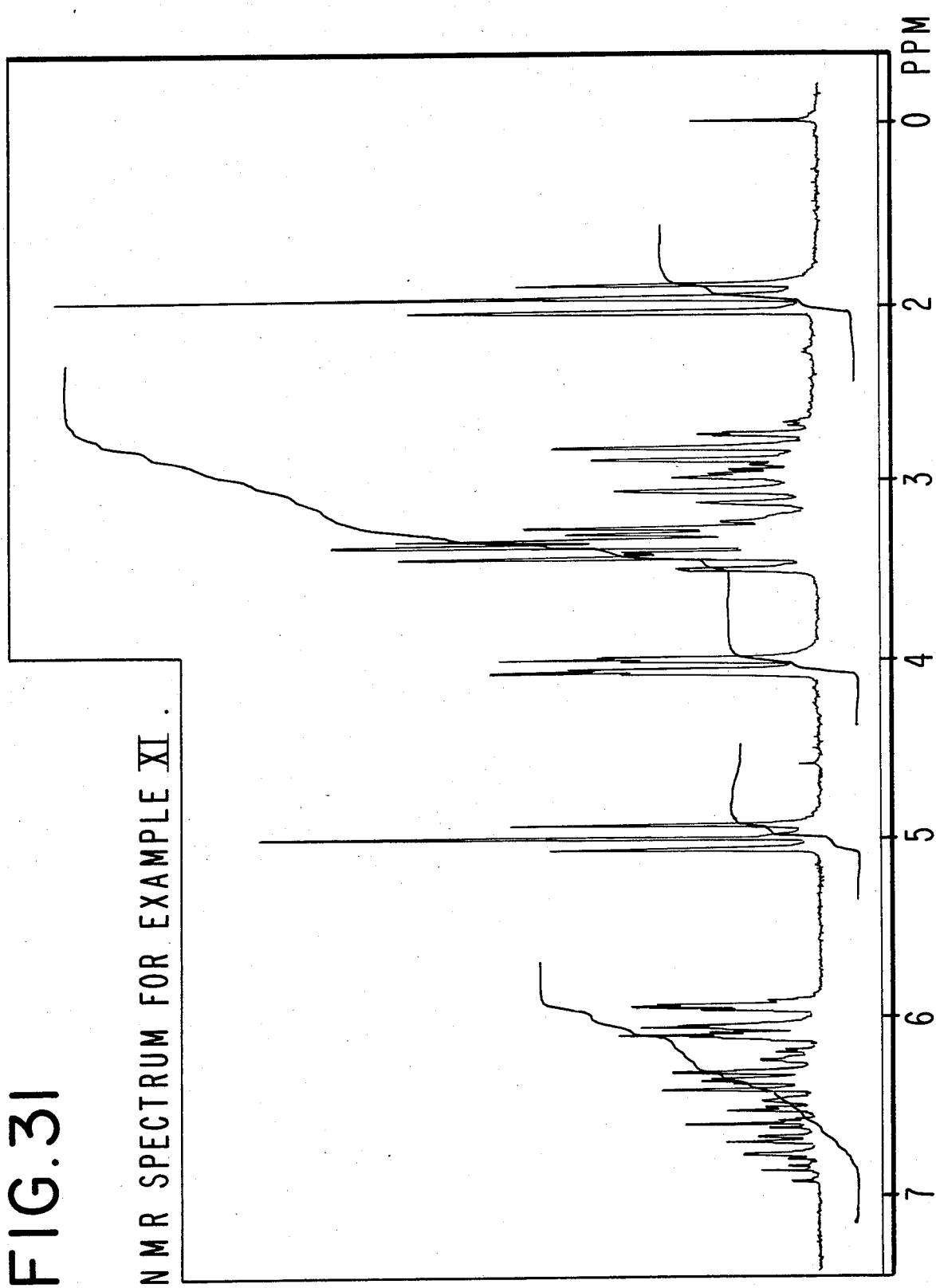
FIG. 31 NMR SPECTRUM FOR EXAMPLE XI.

ESTERS OF ALKYLTHIOALKANOIC ACIDS

BACKGROUND OF THE INVENTION

The present invention describes esters of alkylthioalkanoic acids defined according to the structure:

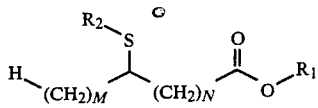

wherein $R_1$ represents $C_3$–$C_6$ alkenyl or $C_1$–$C_4$ alkyl; $R_2$ represents $C_3$ alkyl; $C_3$ hydroxyalkyl or $C_3$ alkenyl; N represents 0, 1 or 2 and M represents 0 or 1 and uses thereof in augmenting or enhancing the aroma or taste of foodstuffs.

Artificial flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variation due to changes in the quality, type and treatment of the raw materials. Such variation can be reflected in the end product and results in unreliable flavor characteristics and uncertainty as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artifical flavoring agents is that of achieving as nearly as possible a true flavor reproduction. This generally proves to be a difficult task since the mechanism for flavoring development in many foods is not understood. This is notable in products having roasted, sesame, fresh green, oniony, fruity, Lychee-Nut, garlic, strawberry, juicy, mushroom, scallion-like, cashew, Durian, floral, leafy, leek and meaty (mutton) aroma and taste nuances.

Reproduction of roasted, sesame, fresh green, oniony, fruity, Lychee-Nut, garlic, strawberry, juicy, mushroom, scallion-like, cashew, Durian, floral, leafy, leek and meaty (mutton) aroma and taste nuances has been the subject of a long and continuous search by those engaged in the production of foodstuffs. The severe shortage of food, especially protein foods, in many parts of the world has given rise to the need for utilizing non-meat sources of proteins and making such proteins as palatable as possible. Hence, materials which will closely simulate or exactly reproduce the flavor and aroma of meat, bread, garlic, onion, mushroom, scallion, cashew and roasted nut are required.

Moreover, there are a great many meat containing or meat based foods presently distributed in a preserved form. Examples of these are condensed soups, dry soup mixes, dry meat, freeze dried or lyophilized meats, packaged gravies and the like. While these products contain meat or meat extracts, the aroma, taste and other organoleptic factors are often impaired by the processing operation and it is desirable to supplement or enhance the flavors of these preserved foods with versatile materials which have meat (mutton), roasted, onion, garlic and mushroom aroma and taste nuances.

Food flavors in the alkylthioalkanoic acid ester area are known in the prior art. Thus, various 4-(methylthio)-butanoic acid ester derivatives defined according to the structure:

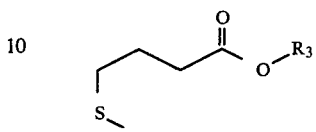

wherein $R_3$ is lower alkyl are known for augmenting or enhancing the aroma or taste of foodstuffs and other consumable materials as is taught in U.S. Pat. No. 3,870,800 issued on Mar. 11, 1975 (the specification of which is incorporated by reference herein). Thus, in Example XVII at columns 13 and 14 of U.S. Pat. No. 3,870,800 the use of ethyl 4-(methylthio)butyrate is shown to be added to a cooked cheese sauce at the rate of 0.5 ppm. The resulting cheese aroma in heated milk is increased adding notes which are usually present in surface-ripened cheese. It is further stated that the cheese flavor intensity is increased. In Example XVIII, at column 14 of U.S. Pat. No. 3,870,800, it is further indicated that methyl 4-(methylthio)butyrate when added to a beef broth increases the meat character and enhances the spice note. Methyl 4-(methylthio)butyrate is shown in Example XIX of U.S. Pat. No. 3,870,800 to enhance the fish flavor of a prepared New England clam chowder when added at the rate of 4 ppm.

German Offenlegungsschrift No. 3307166 (Cyronak, et al) corresponding to U.S. application for U.S. Pat. No. 360,857 filed on Mar. 22, 1982 relates to a foodstuff comprising an amount of compound having the structure:

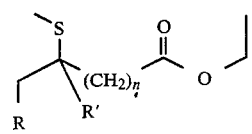

wherein R and R' independent is either hydrogen or an alkyl group of from 1 to 3 carbon atoms and n is either 0 or 1. It is disclosed in German Offenlegungsschrift No. 3307166 that when one of the compounds having the structure:

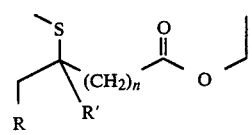

is employed in the foodstuff, it enhances the fruity or vegetable flavor of the foodstuff or augments a green pine needle or fruity flavor in the foodstuff.

However, nothing in the prior art discloses the esters of alkylthioalkanoic acids of our invention having the structure:

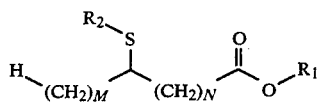

wherein $R_1$ represents $C_3$–$C_6$ alkenyl or $C_1$–$C_4$ alkyl; $R_2$ represents $C_3$ alkyl; $C_3$ hydroxyalkyl or $C_3$ alkenyl; N represents 0, 1 or 2 and M represents 0 or 1 and uses thereof in augmenting or enhancing flavors. Furthermore, nothing in the prior art infers or states anything about the unexpected, unobvious and advantageous properties in augmenting or enhancing food flavors of the esters of alkylthioalkanoic acids of our invention.

BRIEF DESCRIPTION OF THE DRAWINGS

FIG. 1 is the GLC profile for Fraction 5 of the distillation of the reaction product of Example I containing the compound having the structure:

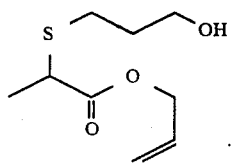

Figure 2:
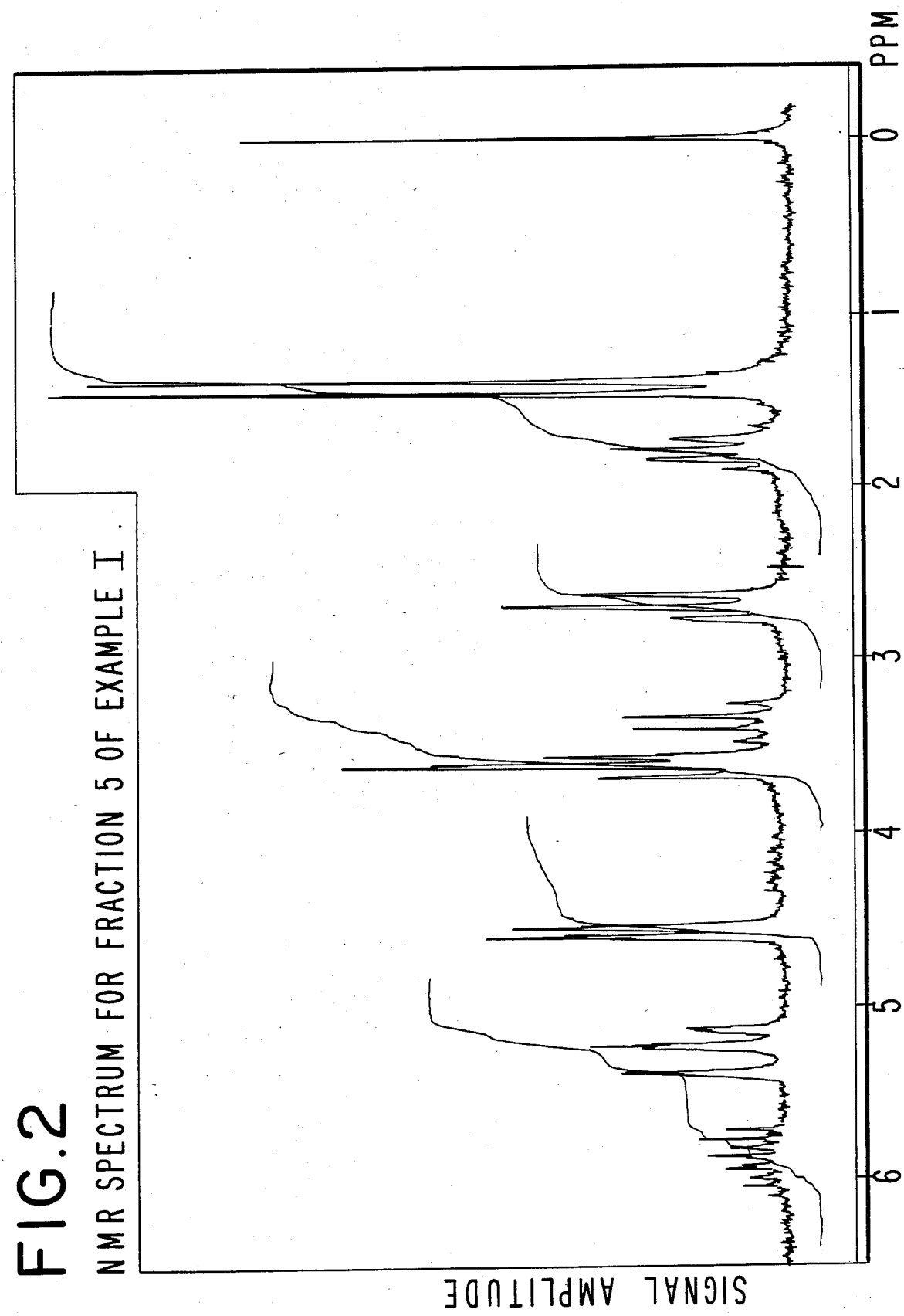

FIG. 2 is the NMR spectrum for Fraction 5 of the distillation of the reaction product of Example I containing the compound having the structure:

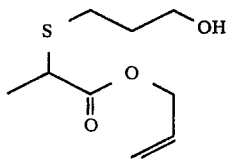

(Conditions: Field strength: 100 MHz; Solvent: $CFCl_3$).

FIG. 3 is the GLC profile for the crude reaction product of Example II containing the compound having the structure:

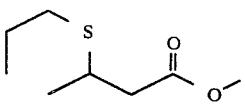

(Conditions: 10'×0.125" SE-30 column programmed at 100°–220° C. at 8° C. per minute).

FIG. 3A is the GLC profile for Fraction 5 of the distillation of the reaction product of Example II containing the compound having the structure:

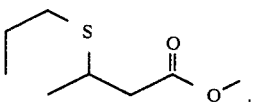

FIG. 4 is the NMR spectrum for Fraction 5 of the distillation of the reaction product of Example II containing the compound having the structure:

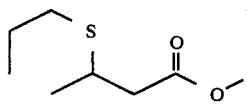

(Conditions: Field strength: 100 MHz; Solvent: $CFCl_3$).

FIG. 5 is the GLC profile for the crude reaction product of Example III containing the compound having the structure:

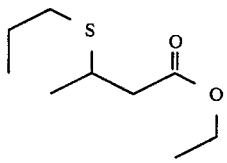

(Conditions: 10'×0.125" SE-30 column programmed at 100°–220° C. at 8° C. per minute).

Figure 6:
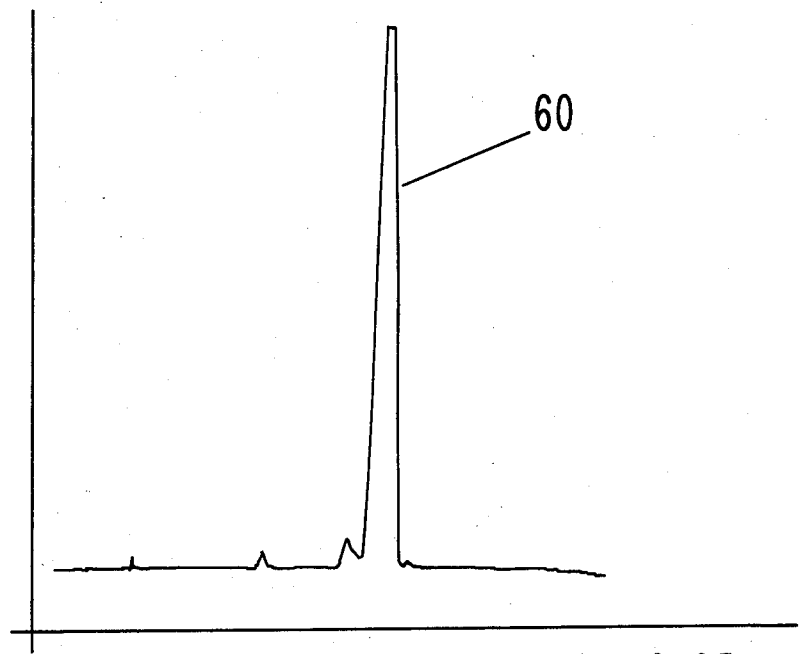

FIG. 6 is the GLC profile for Fraction 6 of the distillation of the reaction product of Example III containing the compound having the structure:

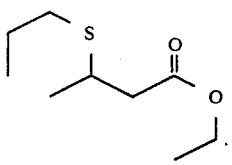

FIG. 7 is the NMR spectrum for Fraction 6 of the distillation of the reaction product of Example III containing the compound having the structure:

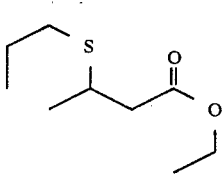

(Conditions: Field strength: 100 MHz; Solvent: $CFCl_3$).

Figure 8:
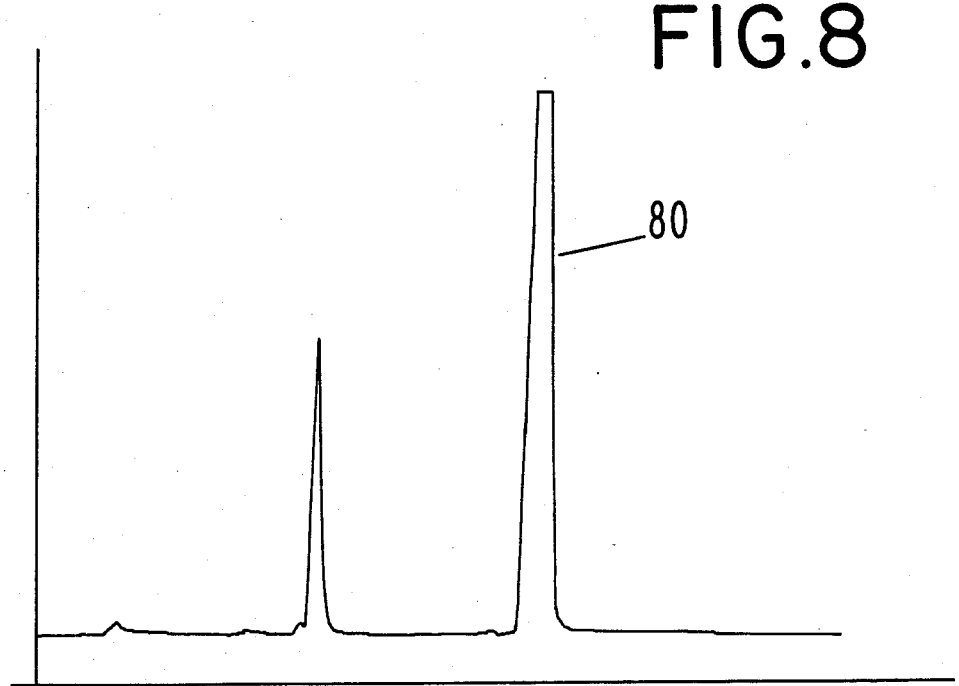

FIG. 8 is the GLC profile for the crude reaction product of Example IV containing the compound having the structure:

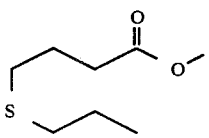

(Conditions: 10'×0.125" carbowax column programmed at 100°–220° C. at 8° C. per minute).

Figure 9:
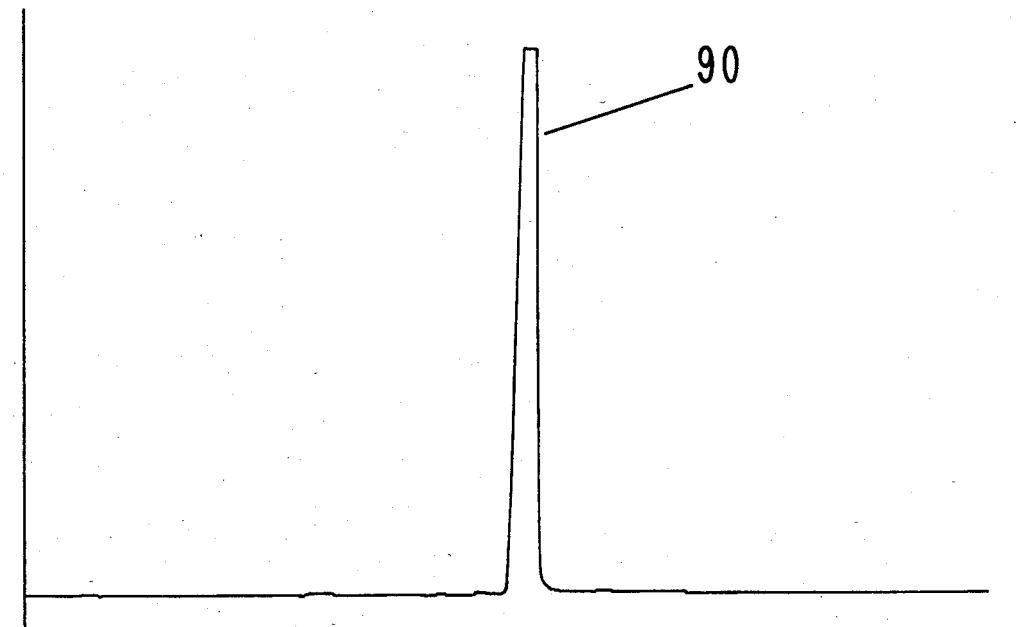

FIG. 9 is the GLC profile for Fraction 6 of the distillation of the reaction product of Example IV containing the compound having the structure:

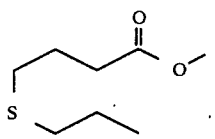

FIG. 10 is the NMR spectrum for Fraction 6 of the distillation of the reaction product of Example IV containing the compound having the structure:

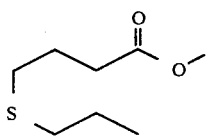

(Conditions: Field strength: 100 MHz; Solvent: CFCl₃).

Figure 11:
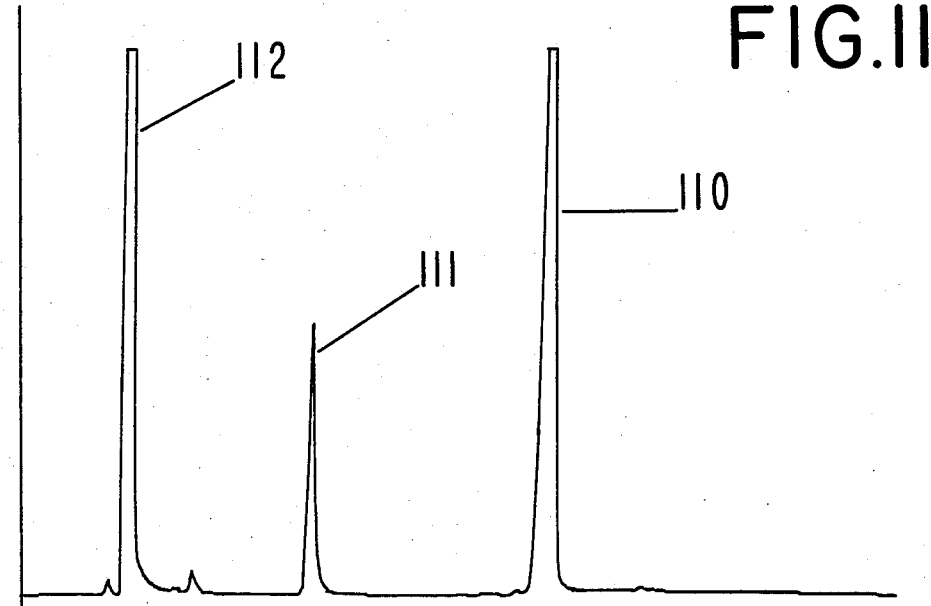

FIG. 11 is the GLC profile for the crude reaction product of Example V containing the compound having the structure:

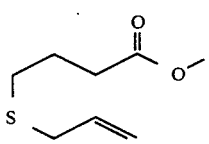

(Conditions: 10'×0.125" carbowax column programmed at 100°–220° C. at 8° C. per minute).

FIG. 12 is the GLC profile for Fraction 10 of the distillation of the reaction product of Example V containing the compound having the structure:

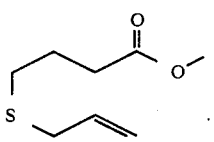

FIG. 13 is the NMR spectrum for Fraction 9 of the distillation of the reaction product of Example V containing the compound having the structure:

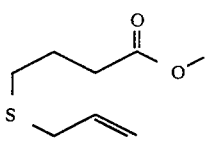

(Conditions: Field strength: 100 MHz; Solvent: CFCl₃).

FIG. 14 is the GLC profile for the crude reaction product of Example VI containing the compound having the structure:

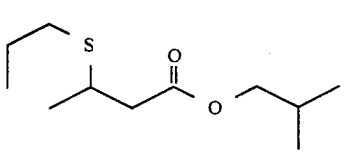

(Conditions: 10'×0.125" SE-30 column).

FIG. 15 is the GLC profile for Fraction 4 of the distillation of the reaction product of Example VI containing the compound having the structure:

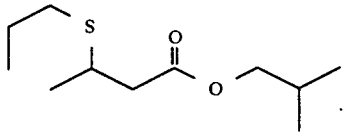

FIG. 16 is the NMR spectrum for Fraction 4 of the distillation of the reaction product of Example VI containing the compound having the structure:

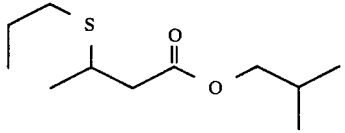

(Conditions: Field strength: 100 MHz; Solvent: CFCl₃).

FIG. 17 is the GLC profile for the crude reaction product of Example VII containing the compound having the structure:

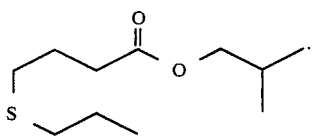

Figure 18:
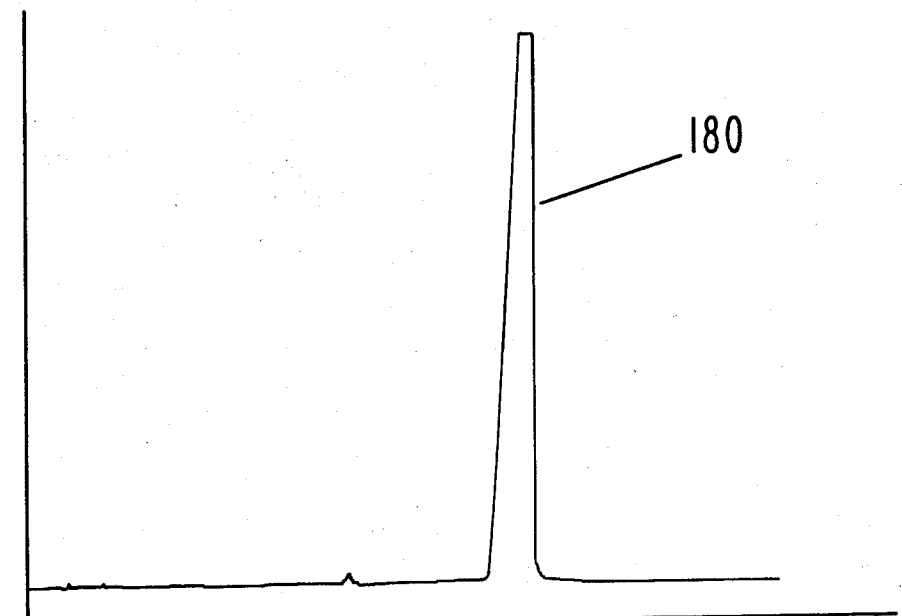

FIG. 18 is the GLC profile for Fraction 5 of the distillation of the reaction product of Example VII containing the compound having the structure:

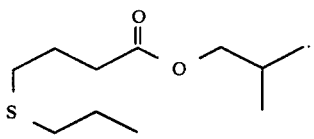

FIG. 19 is the NMR spectrum for Fraction 5 of the distillation product of the reaction product of Example VII containing the compound having the structure:

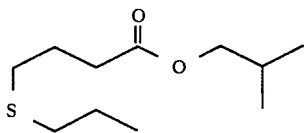

(Conditions: Field strength: 100 MHz; Solvent: CFCl₃).

Figure 20:
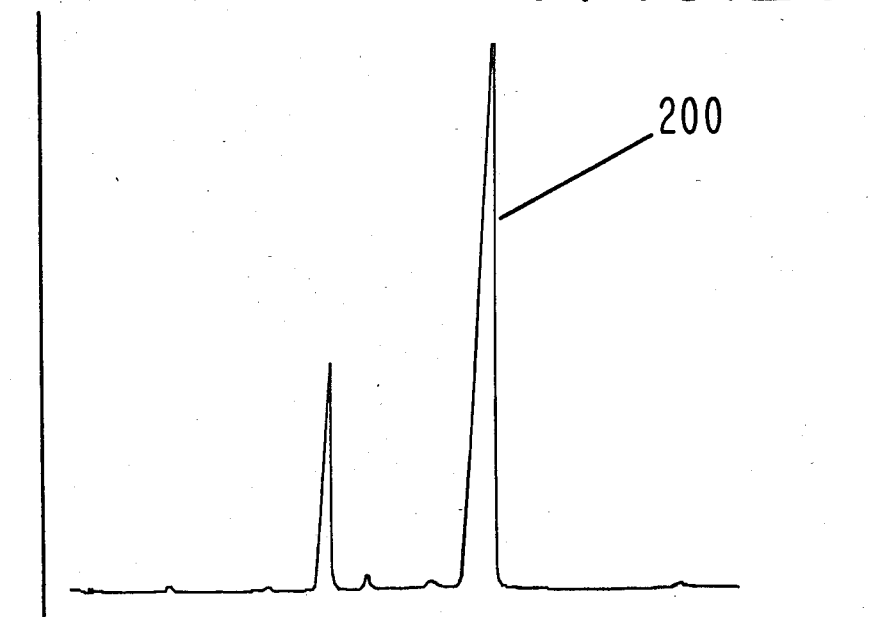

FIG. 20 is the GLC profile for the crude reaction product of Example VIII containing the compound having the structure:

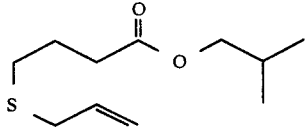

(Conditions: 10'×0.125" SE-30 column programmed at 100°–220° C. at 8° C. per minute).

Figure 21:
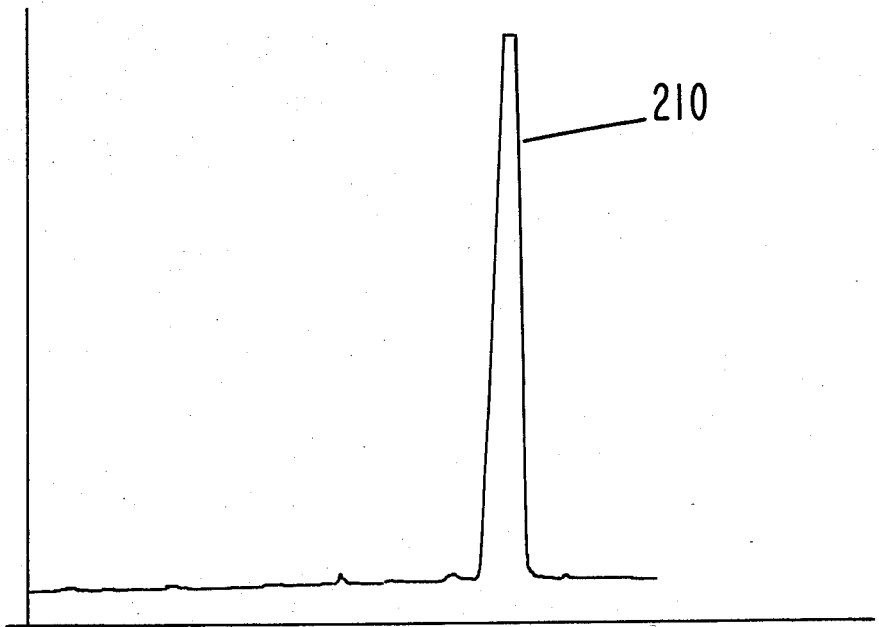

FIG. 21 is the GLC profile for Fraction 4 of the distillation of the reaction product of Example VIII containing the compound having the structure:

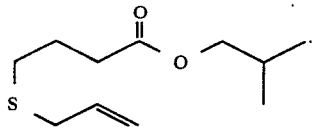

FIG. 22 is the NMR spectrum for Fraction 4 of the distillation of the reaction product of Example VIII containing the compound having the structure:

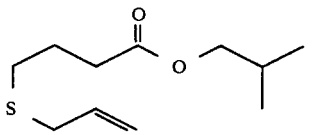

(Conditions: Field strength: 100 MHz; Solvent: CFCl$_3$).

Figure 23:
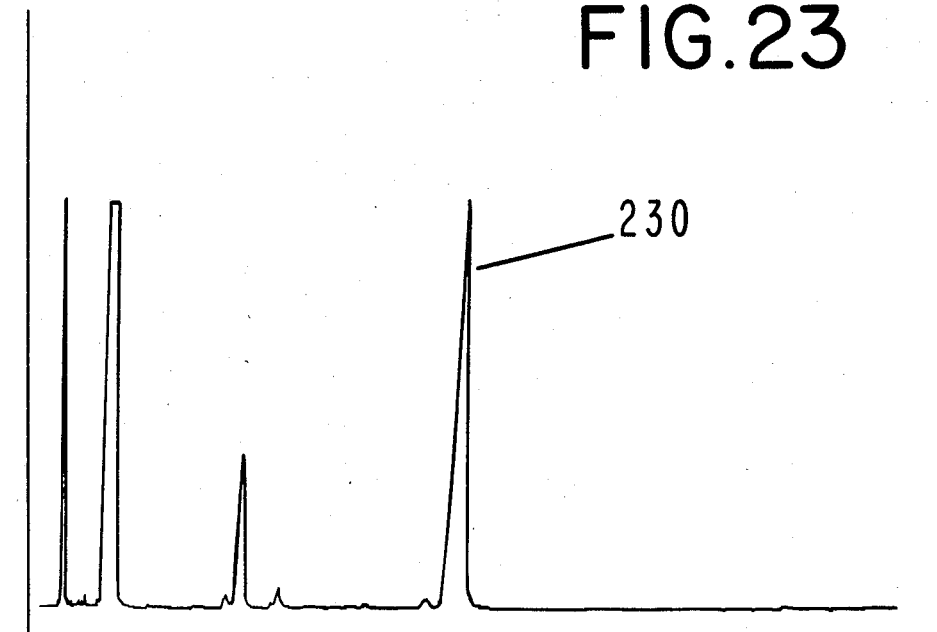

FIG. 23 is the GLC profile for the crude reaction product of Example IX containing the compound having the structure:

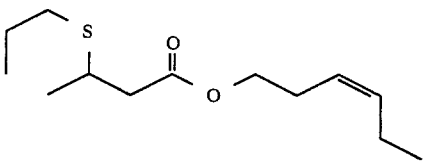

(Conditions: 10'×0.125" SE-30 column programmed at 100°-220° C. at 8° C. per minute).

FIG. 24 is the GLC profile for Fraction 5 of the distillation of the reaction product of Example IX containing the compound having the structure:

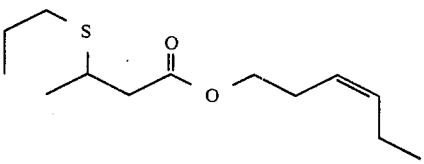

FIG. 25 is the NMR spectrum for Fraction 5 of the distillation of the reaction product of Example IX containing the compound having the structure:

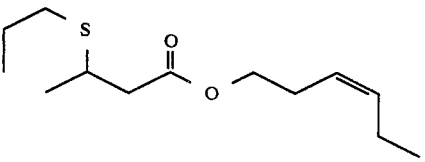

(Conditions: Field strength: 100 MHz; Solvent: CFCl$_3$).

FIG. 26 is the GLC profile for the crude reaction product of Example X containing the compound having the structure:

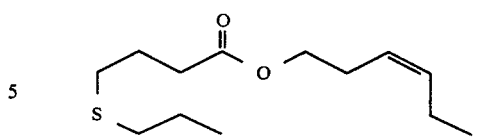

(Conditions: 10'×0.125" SE-30 column programmed at 100°-220° C. at 8° C. per minute).

FIG. 27 is the GLC profile for Fraction 4 of the distillation of the reaction product of Example X containing the compound having the structure:

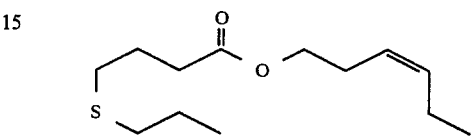

(Conditions: 10'×0.125" SE-30 column programmed at 100°-220° C. at 8° C. per minute).

FIG. 28 is the NMR spectrum for Fraction 4 of the distillation of the reaction product of Example X containing the compound having the structure:

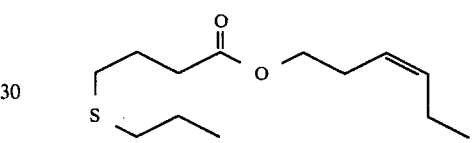

(Conditions: Field strength: 100 MHz: Solvent: CFCl$_3$).

FIG. 29 is the GLC profile for the crude reaction product of Example XI containing the compound having the structure:

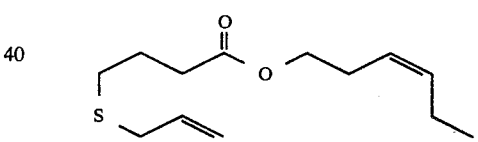

(Conditions: 10'×0.125" SE-30 column programmed at 100°-220° C. at 8° C. per minute).

FIG. 30 is the GLC profile for Fraction 5 of the distillation of the reaction product of Example XI containing the compound having the structure:

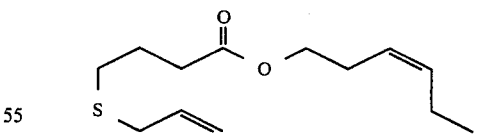

FIG. 31 is the NMR spectrum for Fraction 5 of the distillation of the reaction product of Example XI containing the compound having the structure:

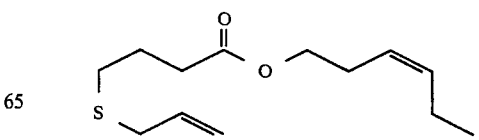

(Conditions: Field strength: 100 MHz; Solvent: CFCl$_3$).

DETAILED DESCRIPTION OF THE DRAWINGS

FIG. 1 is the GLC profile for Fraction 5 of the distillation of the reaction product of Example I containing the compound having the structure:

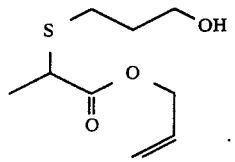

The peak indicated by reference numeral 10 is the peak for the compound having the structure:

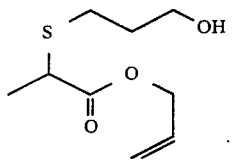

FIG. 3 is the GLC profile for the crude reaction product of Example II containing the compound having the structure:

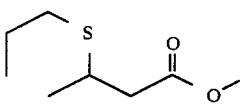

(Conditions: 10'×0.125" SE-30 column programmed at 100°–220° C. at 8° C. per minute). The peak indicated by reference numeral 30 is the peak for the compound having the structure:

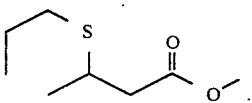

FIG. 3A is the GLC profile for Fraction 5 of the distillation of the reaction product of Example II containing the compound having the structure:

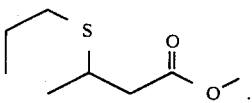

The peak indicated by reference numeral 31 is the peak for the compound having the structure:

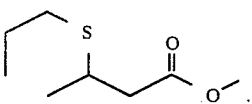

FIG. 5 is the GLC profile for the crude reaction product of Example III containing the compound having the structure:

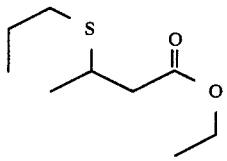

(Conditions: 10'×0.125" SE-30 column programmed at 100°–220° C. at 8° C. per minute). The peak indicated by reference numeral 50 is the peak for the compound having the structure:

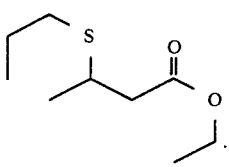

The peak indicated by reference numeral 51 is the peak for the reactant, ethyl crotonate. The peak indicated by reference numeral 52 is the peak for the reactant, n-propyl mercaptan.

FIG. 6 is the GLC profile for Fraction 6 of the distillation product of the reaction product of Example III containing the compound having the structure:

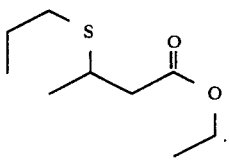

The peak indicated by reference numeral 60 is the peak for the compound having the structure:

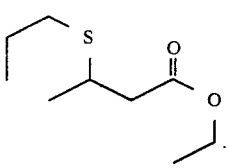

FIG. 8 is the GLC profile for the crude reaction product of Example IV containing the compound having the structure:

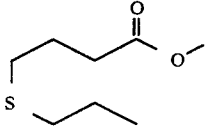

(Conditions: 10'×0.125" carbowax column programmed at 100°–220° C. at 8° C. per minute). The peak indicated by reference numeral 80 is the peak for the compound having the structure:

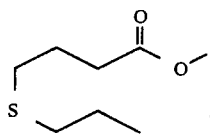

FIG. 9 is the GLC profile for Fraction 6 of the distillation of the reaction product of Example IV containing the compound having the structure:

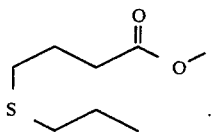

The peak indicated by reference numeral 90 is the peak for the compound having the structure:

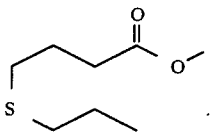

FIG. 11 is the GLC profile for the crude reaction product of Example V containing the compound having the structure:

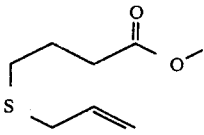

(Conditions: 10′×0.125″ carbowax column programmed at 100°–220° C. at 8° C. per minute). The peak indicated by reference numeral 110 is the peak for the compound having the structure:

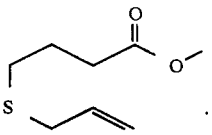

The peak indicated by reference numeral 111 is the peak for the reactant having the structure:

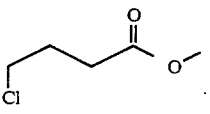

The peak indicated by reference numeral 112 is the peak for the extraction solvent, methylene dichloride.

FIG. 14 is the GLC profile for the crude reaction product of Example VI containing the compound having the structure:

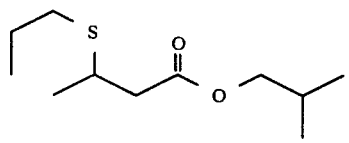

(Conditions: 10′×0.125″ SE-30 column). The peak indicated by reference numeral 140 is the peak for the compound having the structure:

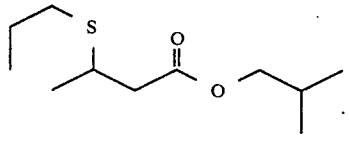

FIG. 15 is the GLC profile for Fraction 4 of the distillation of the reaction product of Example VI containing the compound having the structure:

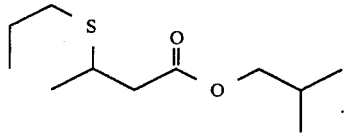

The peak indicated by reference numeral 150 is the peak for the compound having the structure:

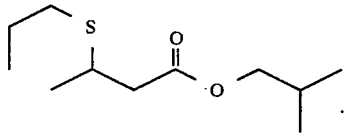

FIG. 17 is the GLC profile for the crude reaction product of Example VII containing the compound having the structure:

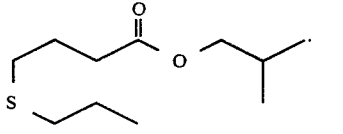

The peak indicated by reference numeral 170 is the peak for the compound having the structure:

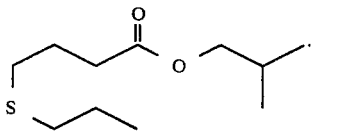

FIG. 18 is the GLC profile for Fraction 5 of the distillation of the reaction product of Example VII containing the compound having the structure:

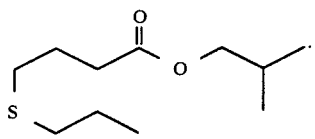

The peak indicated by reference numeral 180 is the peak for the compound having the structure:

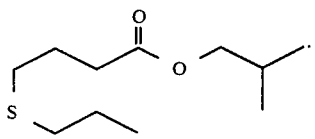

FIG. 20 is the GLC profile for the crude reaction product of Example VIII containing the compound having the structure:

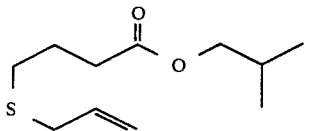

(Conditions: 10'×0.125" SE-30 column programmed at 100°-220° C. at 8° C. per minute). The peak indicated by reference numeral 200 is the peak for the compound having the structure:

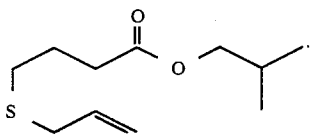

FIG. 21 is the GLC profile for Fraction 4 of the distillation of the reaction product of Example VIII containing the compound having the structure:

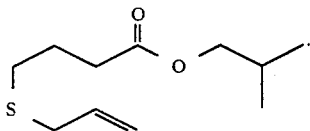

The peak indicated by reference numeral 210 is the peak for the compound having the structure:

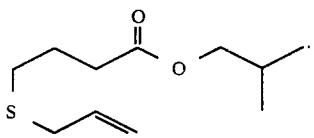

FIG. 23 is the GLC profile for the crude reaction product of Example IX containing the compound having the structure:

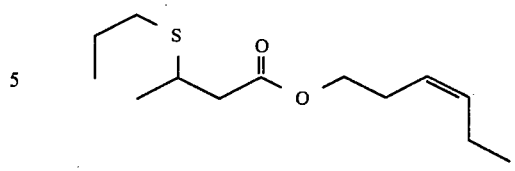

(Conditions: 10'×0.125" SE-30 column programmed at 100°-220° C. at 8° C. per minute). The peak indicated by reference numeral 230 is the peak for the compound having the structure:

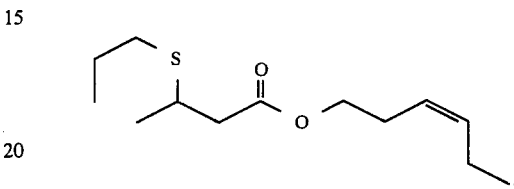

FIG. 24 is the GLC profile for Fraction 5 of the distillation of the reaction product of Example IX containing the compound having the structure:

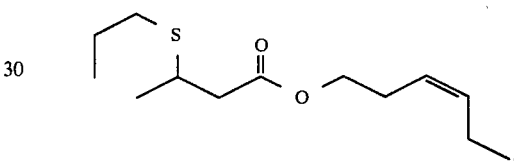

The peak indicated by reference numeral 240 is the peak for the compound having the structure:

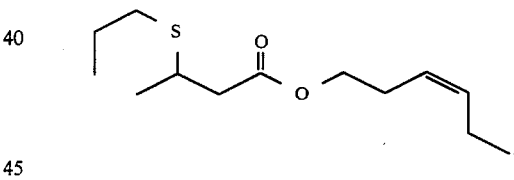

FIG. 26 is the GLC profile for the crude reaction product of Example X containing the compound having the structure:

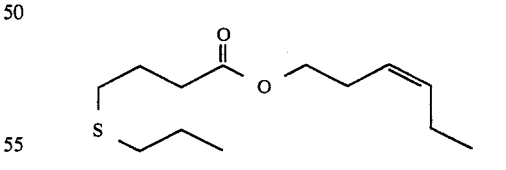

(Conditions: 10'×0.125" SE-30 column programmed at 100°-220° C. at 8° C. per minute). The peak indicated by reference numeral 260 is the peak for the compound having the structure:

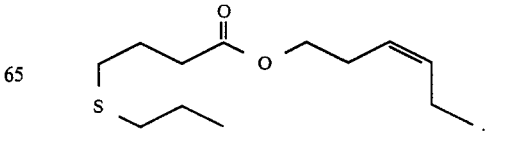

FIG. 27 is the GLC profile for Fraction 4 of the distillation of the reaction product of Example X containing the compound having the structure:

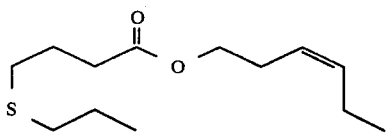

(Conditions: 10'×0.125" SE-30 column programmed at 100°–220° C. at 8° C. per minute). The peak indicated by reference numeral 270 is the peak for the compound having the structure:

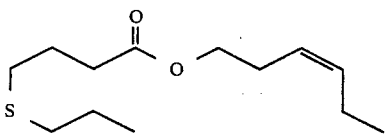

FIG. 29 is the GLC profile for the crude reaction product of Example XI containing the compound having the structure:

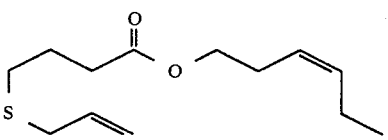

(Conditions: 10'×0.125" SE-30 column). The peak indicated by reference numeral 290 is the peak for the compound having the structure:

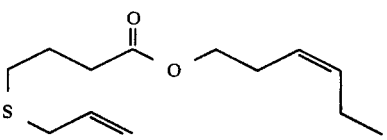

FIG. 30 is the GLC profile for Fraction 5 of the distillation of the reaction product of Example XI containing the compound having the structure:

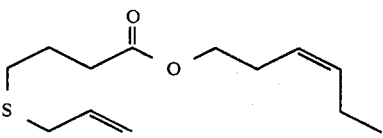

The peak indicated by reference numeral 300 is the peak for the compound having the structure:

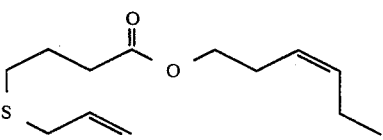

THE INVENTION

The present invention provides esters of alkylthioalkanoic acids useful for augmenting or enhancing the aroma or taste of foodstuffs, said esters of alkylthioalkanoic acids being defined according to the structure:

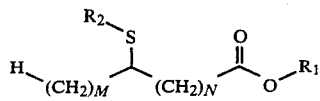

wherein $R_1$ represents $C_3$–$C_6$ alkenyl or $C_1$–$C_4$ alkyl; $R_2$ represents $C_3$ alkyl; $C_3$ hydroxyalkyl or $C_3$ alkenyl; N represents 0, 1 or 2 and M represents 0 or 1, as well as methods for augmenting or enhancing or modifying the organoleptic properties, e.g., taste and aroma of said foodstuffs.

The esters of alkylthioalkanoic acids of our invention augment or enhance roasted, sesame, fresh green, oniony, fruity, Lychee Nut, garlic, strawberry, juicy, mushroom, scallion-like, cashew, Durian, floral, leafy, leek and meaty (mutton) aroma and taste nuances making them useful for augmenting or enhancing flavors for such foodstuffs as roasted nut, bread crust, sesame, coffee, Durian, onion, garlic, strawberry, mushroom, gooseberry, pineapple, cashew, leek and mutton flavored foodstuffs.

The esters of alkylthioalkanoic acids of our invention having the formula:

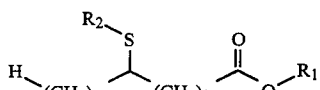

may be produced by reacting a carboxylic acid having the structure:

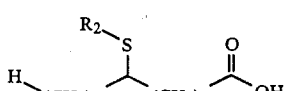

with an alcohol having the formula:

$R_1$—OH according to the reaction:

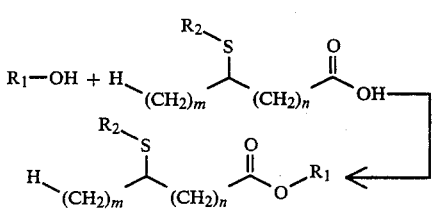

in the presence of a prontonic acid catalyst such as para-toluene sulfonic acid, sulfuric acid, phosphoric acid or methane sulfonic acid or mixtures thereof, e.g., mixtures of methane sulfonic acid and phosphoric acid. The reaction is carried out at reflux conditions, that is, at atmospheric pressure and temperatures of between about 90° C. and 140° C. The preferred mole ratio of alcohol having the formula:

$R_1$—OH to carboxylic acid having the structure:

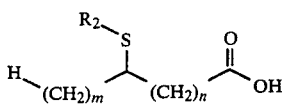

is about 4:1 but may range from about 1:1 alcohol:carboxylic acid up to about 6:1 alcohol:carboxylic acid. The percent protonic acid catalyst in the reaction mass may vary from about 1% up to about 0.1% based on the reaction mass.

A variation of the foregoing process occurs in the reaction of allyl alcohol with 2-mercaptopropionic acid having the structure:

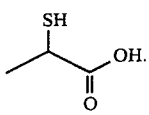

In this reaction the allyl alcohol not only esterifies the carboxylic acid moiety but also adds via the double bond of the allyl alcohol to the mercapto moiety forming a hydroxy propyl mercapto ether according to the reaction:

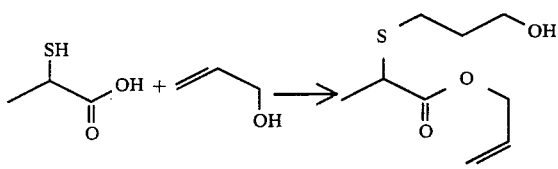

to form the compound having the structure:

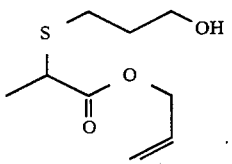

In this reaction the mole ratio of allyl alcohol:mercaptopropionic acid may vary from about 2:1 up to about 6:1 with a preferred mole ratio of 4:1. The preferred catalyst is para-toluene sulfonic acid although other protonic acid catalysts can be used, for example, phosphoric acid, sulfuric acid, methane sulfonic acid, and xylene sulfonic acid. The amount of catalyst may vary from about 0.1% up to about 1.0% by weight of the reaction mass. The reaction is carried out under reflux conditions, e.g., from about 80° C. up to about 140° C. preferably at atmospheric pressure. The reaction time may vary from about 1 hour up to about 12 hours. At the end of the reaction, the reaction mass is "worked up" and finally fractionally distilled. In this "work up" the reaction mass is first extracted using an inert solvent such as methylene dichloride. The methylene dichloride extract is then washed with aqueous base such as aqueous sodium carbonate followed by aqueous sodium chloride and then dried on a drying material such as anhydrous sodium sulfate. The resulting mixture is then filtered and finally distilled on a fractional distillation column to yield the reaction product having the structure:

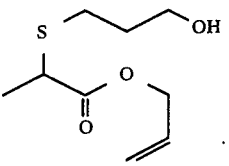

The esters of alkylthioalkanoic acids defined according to the generic structure:

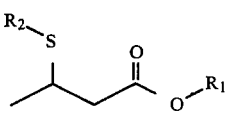

may also be prepared by reacting a mercaptan having the structure:

$R_2$—SH with an ester of crotonic acid having the structure:

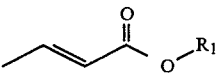

according to the reaction:

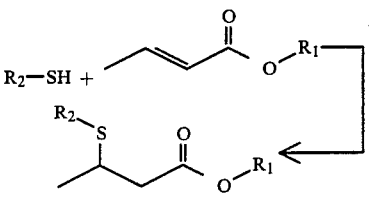

This reaction takes place in the presence of an ultra-violet light source. The temperature of reaction may vary from about 20° C. up to about 40° C. The mole ratio of crotonic acid ester:mercaptan may vary from about 1:2 up to about 2:1 with a preferred mole ratio of about 1:1. The reaction time may vary from about 1 hour up to about 12 hours. At the end of the reaction, the reaction mass is "worked up" as set forth, supra. The "worked up" reaction mass is then fractionally distilled on a fractional distillation apparatus to yield foodgrade product having the structure:

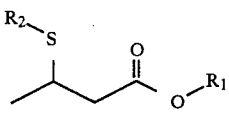

wherein $R_1$ and $R_2$ are defined, supra.

The genus of compounds having the structure:

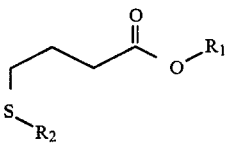

may be prepared by reacting a mercaptan having the structure:

R₂—SH with a 4-halo butanoic acid ester having the structure:

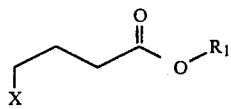

wherein X represents chloro or bromo according to the reaction:

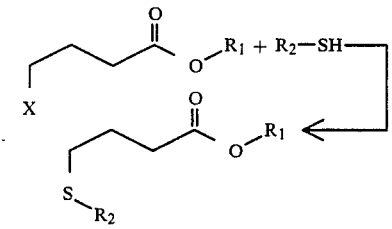

This reaction takes place in the presence of an alkali metal alkoxide catalyst or aluminum isopropoxide. Examples of alkali metal alkoxide catalyst are sodium methoxide, sodium ethoxide, sodium-n-propoxide, potassium methoxide, potassium ethoxide and potassium isobutoxide and potassium t-butoxide. The reaction temperature may vary from about 30° C. up to about 50° C. The reaction time may vary from about 1 hour up to about 12 hours. The mole ratio of mercaptan having the structure:

R₂—SH to halo butanoic acid ester having the structure:

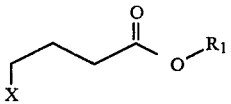

may vary from about 1.5:1 up to about 1:1.5 with a preferred mole ratio of 1:1. The aluminum isopropoxide or alkali metal alkoxide used is carried into the reaction mass in the form of a solution, e.g., sodium methoxide in methyl alcohol, preferably in a 25% solution of methyl alcohol. The mole ratio of alkali metal alkoxide or aluminum isopropoxide:reactants may vary from about 1:10 up to about 1:4 based on solvent-free alkali metal alkoxide. At the end of the reaction, the reaction mass is "worked up" by extracting same with an inert solvent such as methylene dichloride and drying the extract over anhydrous sodium sulfate or the like. The resulting mixture is then filtered and distilled on a fractional distillation column to yield foodgrade product having the generic structure:

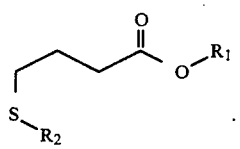

The esters of alkylthioalkanoic acids of our invention may also be formed by means of an "ester interchange" reaction whereby a first ester having the structure:

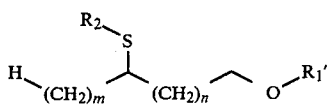

is reacted with an alcohol having the structure:

R₁—OH according to the reaction:

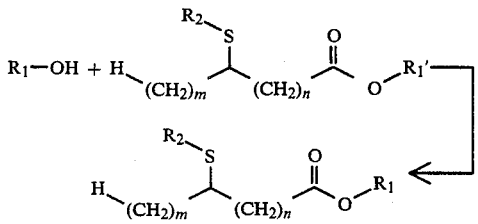

This ester interchange reaction takes place at reflux conditions in the presence of a protonic acid catalyst such as para-toluene sulfonic acid, xylene sulfonic acid, methane sulfonic acid, phosphoric acid, sulfuric acid or mixtures of two or more of the foregoing, e.g., mixtures of methane sulfonic acid and phosphoric acid. The mole ratio of alcohol:ester having the structure:

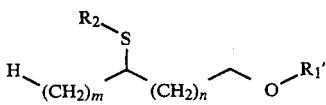

may vary from about 1:1 up to about 6:1 with a preferred mole ratio of alcohol:ester being about 4:1. The percent of protonic acid catalyst in the reaction mass, based on the reaction mass is from about 0.1% up to about 1%. The reaction temperature at reflux may vary from about 80° C. up to about 140° C. and the reaction preferably takes place at atmospheric pressure. The reaction time may vary from about 1 hour up to about 12 hours.

Examples of the esters of alkylthioalkanoic acids of our invention and their organoleptic properties are as follows:

TABLE I

| Structure of Compound | Organoleptic Properties |
|---|---|
| The compound having the structure: | A roasted, sesame aroma and taste profile at 2 ppm causing |

TABLE I-continued

| Structure of Compound | Organoleptic Properties |
|---|---|
| 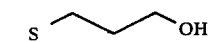<br>prepared according to Example I. | it to be useful in roasted nut, bread crust, sesame and coffee flavored foodstuffs. |
| The compound having the structure:<br>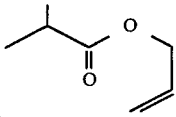<br>prepared according to Example II. | A fresh, green, oniony, fruity, Lychee Nut aroma and taste profile at 2 ppm causing it to be useful in Durian and onion flavored foodstuffs. |
| The compound having the structure:<br><br>prepared according Example III. | A fresh, green, oniony, fruity and garlic aroma and taste profile at 1 ppm causing it to be useful in onion and garlic flavored foodstuffs. |
| The compound having the structure:<br>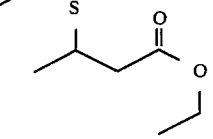<br>prepared according to Example IV. | A green, strawberry, juicy, mushroom and scallion-like aroma and taste profile at 1 ppm causing it to be useful in strawberry, mushroom and gooseberry flavored foodstuffs. |
| The compound having the structure:<br>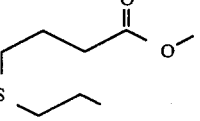<br>prepared according to Example V. | A cashew and Durian aroma and taste profile at 0.01 ppm causing it to be useful in pineapple, cashew, Durian and roasted nut (almond, cashew and hazel nut) flavored foodstuffs. |
| The compound having the structure:<br>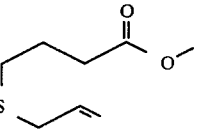<br>prepared according to Example VI. | A green and oniony aroma and taste profile at 2 ppm causing it to be useful in onion flavored foodstuffs. |
| The compound having the structure:<br>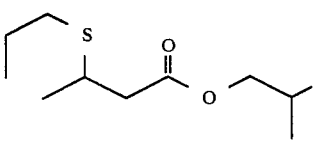<br>prepared according to Example VII. | A green and oniony aroma and taste profile at 5 ppm causing it to be useful in onion flavored foodstuffs. |
| The compound having | A green and floral aroma |

TABLE I-continued

| Structure of Compound | Organoleptic Properties |
|---|---|
| the structure: [ethyl 3-(allylthio)... isobutyl ester structure] prepared according to Example VIII. | and taste profile at 2 ppm causing it to be useful in Kiwi flavored foodstuffs. |
| The compound having the structure: [propylthio methyl-substituted ester with cis-hexenyl group] prepared according to Example IX. | A roasted onion and garlic aroma and taste profile at 1 ppm causing it to be useful in onion and garlic flavored foodstuffs. |
| The compound having the structure: [allylthio alkanoate with cis-hexenyl ester] prepared according to Example X. | A green, leafy, leek and oniony aroma and taste profile at 5 ppm causing it to be useful in leek-flavored foodstuffs. |
| The compound having the structure: [allylthio alkanoate with cis-hexenyl ester variant] prepared according to Example XI. | A meaty (mutton-like) aroma and taste profile at 2 ppm causing it to be useful in mutton and "lamb-chop" flavored foodstuffs. |

Thus, the esters of alkylthioalkanoic acids of our invention can be used to alter, vary, fortify, modify, enhance or otherwise improve the organoleptic properties, including flavor and/or aroma of a wide variety of materials which are ingested, consumed or otherwise organoleptically sensed.

The term "alter" in its various forms will be understood herein to mean the supplying or imparting of a flavor character or note to an otherwise bland, relatively tasteless substance or augmenting an existing flavor characteristic where the natural flavor is deficient in some regard or supplementing the existing flavor or aroma impression to modify the organoleptic character. The materials which are so altered are generally referred to herein as consumable materials.

Such esters of alkylthioalkanoic acids of our invention are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetable, cereals, soft drinks, snack foods, dog and cat foods, other veterinary products, and the like.

When the esters of alkylthioalkanoic acids according to this invention are used in a food flavoring composition, they can be combined with conventional flavoring materials or adjuvants. Such co-ingredients or flavoring adjuvants are well known in the art for such use and have been extensively described in the literature. Apart from the requirement that any adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers.

Examples of preferred co-flavoring adjuvants are:
Methyl thiazole alcohol (4-methyl-5-beta-hydroxyethyl thiazole);
2-Methyl butanethiol;
4-Mercapto-2-butanone;
3-Mercapto-2-pentanone;
1-Mercapto-2-propanone;
Benzaldehyde;
Furfural;

Furfuryl alochol;
2-Mercapto propionic acid;
Alkyl pyrazine;
Methyl pyrazine;
2-Ethyl-3-methyl pyrazine;
Polysulfides;
Dipropyl disulfide;
Methyl benzyl disulfide;
Alkyl thiophenes;
2-Butyl thiophene;
2-3-Dimethyl thiophene;
5-Methyl furfural;
Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Monopotassium glutamate;
Sulphur-containing amino acids, e.g., cysteine;
Hydrolyzed vegetable protein;
2-Methylfuran-3-thiol;
2-Methyldihydrofuran-3-thiol;
2,5-dimethylfuran-3-thiol;
Hydrolyzed fish protein;
Tetramethyl pyrazine;
Allyl propyl disulfide;
Allyl propyl trisulfide;
Propyl propenyl disulfide;
Propyl propenyl trisulfide;
Propenyl allyl disulfide;
Propenyl allyl trisulfide;
Methyl propyl disulfide;
Methyl propyl trisulfide; and
Methyl-2-butenyl trisulfide.

The esters of alkylthioalkanoic acids or the compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carrageenan, other gums and the like. The esters of alkylthioalkanoic acids according to this invention can be incorporated with the carriers by conventional means such as spray-drying, drum-drying and the like. Such carriers can also include materials for coacervating the esters of alkylthioalkanoic acids (and other flavoring ingredients, as present) to provide encapsulated products. When the carrier is an emulsion, the flavoring composition can also contain emulsifiers such as mono- and diglycerides or fatty acids and the like. With these carriers or vehicles, the desired physical form of the composition can be prepared.

The esters of alkylthioalkanoic acids utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodstuff; and further process or treatment steps to which the foodstuff will be subjected; regional and other preference factors; the type of storage, if any, to which the product will be subject; and the preconsumption treatment, such as baking, frying and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate composition contain from about 0.001 parts per million (ppm) to about 250 ppm of esters of alkylthioalkanoic acids or mixtures thereof. More particularly, in food compositions it is desirable to use from about 0.001 ppm to 100 ppm for enhancing flavors and in certain preferred embodiments of the invention, from about 0.001 to 50 ppm of the derivatives are included to add positive flavors to the finished product.

The esters of alkylthioalkanoic acids of our invention to be utilized in flavoring compositions can be varied over a wide range depending upon the particular quality to be added to the foodstuff. Thus, amounts of one or more derivatives according to the present invention of from about 0.05 ppm up to 80 or 90 percent of the total flavoring composition can be incorporated in such compositions. It is generally found to be desirable to include from about 0.05 ppm up to about 0.1 percent of the esters of alkylthioalkanoic acids in such compositions.

The following examples are given to illustrate embodiments of the invention as it is preferred to practice it. It will be understood that these examples are illustrative and the invention is not to be considered as restricted thereto except as indicated in the appended claims.

All parts, proportions, percentages and ratios used herein are by weight unless otherwise indicated.

EXAMPLE I

Preparation of 2(3-Hydroxypropylthio)Propionic Acid, Allyl Ester

Reaction:

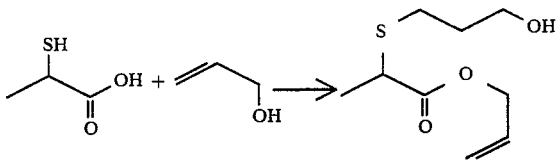

Into a 250 cc reaction flask equipped with stirrer, thermometer, reflux condenser and heating mantle are placed 26.5 grams of 2-mercapto propionic acid (0.25 moles); 58 grams allyl alcohol (1.0 moles) and 0.2 grams of para-toluene sulfonic acid. With stirring, the reaction mass is heated to reflux and maintained at reflux for a period of 8 hours. At the end of the 8 hour period, the reaction mass is cooled to room temperature and transferred to a separatory funnel. The reaction mass is then extracted with two 250 ml portions of methylene dichloride. The methylene dichloride extracts are combined and washed with one 100 ml portion of saturated sodium carbonate solution followed by one 100 ml portion of saturated sodium chloride solution. The resulting organic material is dried over anhydrous sodium sulfate, filtered and distilled on a micro Vigreux column yielding the following fractions:

| Fraction No. | Vapor Temp. (°C.) | Liquid Temp. (°C.) | Vacuum mm/Hg. Pressure |
|---|---|---|---|
| 1 | 32/ | 35/ | 50 |
| 2 | 55 | 60 | 50 |
| 3 | 79 | 85 | 50 |
| 4 | 90 | 119 | 20 |
| 5 | 115 | 144 | 20 |
| 6 | 120 | 160 | 2 |

The reaction product as confirmed by NMR, IR, mass spectral and GLC analyses have the structure:

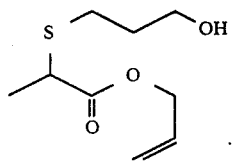

The reaction product has a roasted and sesame aroma and taste profile at 2 ppm causing it to be useful in roasted nut, bread crust, sesame and coffee flavored foodstuffs.

FIG. 1 is the GLC profile for Fraction 5 of the foregoing distillation product. The peak indicated by reference numeral 10 is the peak for the compound having the structure:

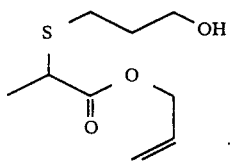

FIG. 2 is the NMR spectrum for Fraction 5 of the foregoing distillation containing the compound having the structure:

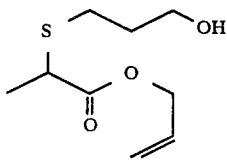

(conditions: Field strength: 100 MHz; Solvent: CFCl₃).

EXAMPLE II

Preparation of Methyl-3-(Propylthio)Butyrate

Reaction:

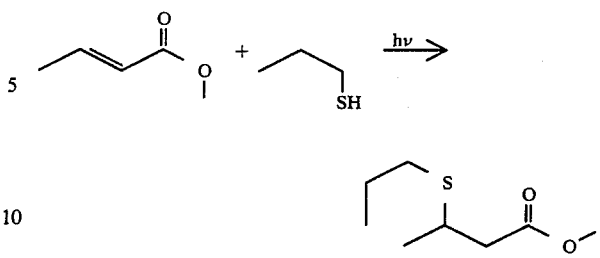

Into a 100 cc reaction flask equipped with stirrer, thermometer, reflux condenser and ultra-violet light source are placed 20 grams of methyl crotonate and 15.2 grams of n-propyl mercaptan (0.2 moles of methyl crotonate and 0.2 moles of n-propyl mercaptan). With stirring, the ultra-violet light is turned on and the reaction mass is maintained at a temperature of 30° C. The reaction mass is exposed with stirring to the ultra-violet light at 30° C. for a period of 4 hours. At the end of the 4 hour period, the reaction mass is transferred to a distillation flask and distilled on a micro Vigreux column yielding the following fractions:

| Fraction No. | Vapor Temp. (°C.) | Liquid Temp. (°C.) | Vacuum mm/Hg. Pressure |
|---|---|---|---|
| 1 | 34/ | 93/ | 25 |
| 2 | 107 | 110 | 25 |
| 3 | 108 | 110 | 25 |
| 4 | 110 | 111 | 25 |
| 5 | 111 | 112 | 25 |
| 6 | 111 | 114 | 25 |
| 7 | 109 | 120 | 25 |

The reaction product has the structure:

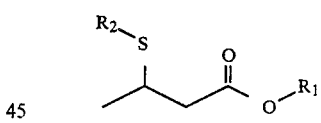

as confirmed by mass spectral, NMR, IR and GLC anaylses.

The reaction product has an aesthetically pleasing fresh, green, oniony, fruity and Lychee Nut aroma and taste profile at 2 ppm causing it to be useful in Durian and onion flavored foodstuffs.

FIG. 3 is the GLC profile for the crude reaction product prior to distillation (Conditions: 10'×0.125" SE-30 column programmed at 100°–220° C. at 8° C. per minute). The peak indicated by reference numeral 30 is the peak for the compound having the structure:

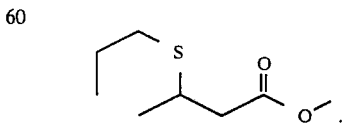

FIG. 3A is the GLC profile for Fraction 5 of the foregoing distillation containing the compound having the structure:

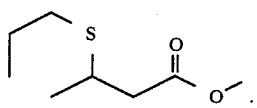

The peak indicated by reference numeral 31 is the peak for the compound having the structure:

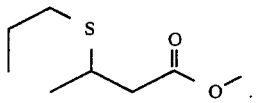

FIG. 4 is the NMR spectrum for Fraction 5 of the foregoing distillation containing the compound having the structure:

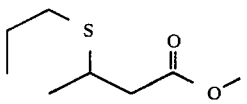

(Conditions: Field strength: 100 MHz; Solvent: CFCl$_3$).

EXAMPLE III

Preparation of Ethyl-3-(Propylthio)Butyrate

Reaction:

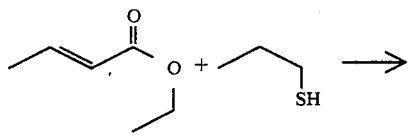

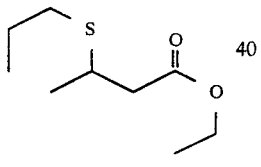

Into a 500 ml one neck flask equipped with reflux condenser, spin bar, and hot plate containing a built in magnetic stirrer, cooling bath and ultra-violet light source are placed 17.9 grams (0.157 moles) of ethyl crotonate and 12 grams (0.158 moles) of n-propyl mercaptan with stirring and maintaining the temperature at 30° C., the reaction mass is stirred after turning the ultra-violet light on. The reaction mass is continued to be stirred for a period of 8 hours. At the end of the 8 hour period, the ultra-violet light was turned off and the reaction mass is transferred to a distillation flask and distilled on a micro Vigreux column yielding the following fractions:

| Fraction No. | Vapor Temp. (°C.) | Liquid Temp. (°C.) | Vacuum mm/Hg. Pressure |
|---|---|---|---|
| 1 | 45/ | 57/ | 25 |
| 2 | 44 | 73 | 25 |
| 3 | 102 | 116 | 25 |
| 4 | 114 | 120 | 25 |
| 5 | 118 | 120 | 25 |
| 6 | 119 | 122 | 25 |
| 7 | 119 | 122 | 25 |
| 8 | 118 | 123 | 25 |
| 9 | 118 | 125 | 25 |
| 10 | 110 | 140 | 25 |

The resulting reaction product has the structure:

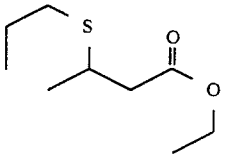

as confirmed by NMR, IR, GLC and mass spectral anaylses.

The resulting compound having the structure;

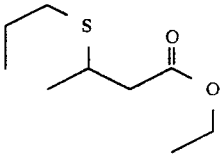

has a fresh, green, oniony, fruity and garlic aroma and taste profile at 1 ppm causing it to be useful in onion and garlic flavored foodstuffs.

FIG. 5 is the GLC profile for the crude reaction product prior to distillation (Conditions: 10'×0.125" SE-30 column programmed at 100°–220° C. at 8° C. per minute). The peak indicated by reference numeral 50 is the peak for the reaction product having the structure:

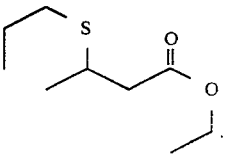

The peak indicated by reference numeral 51 is the peak for the reactant, ethyl crotonate. The peak indicated by reference numeral 52 is the peak for the reactant, n-propyl mercaptan.

FIG. 6 is the GLC profile for Fraction 6 of the foregoing distillation. The peak indicated by reference numeral 60 is the peak for the reaction product having the structure:

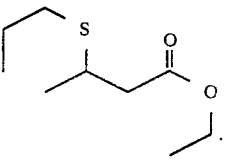

FIG. 7 is the NMR spectrum for Fraction 6 of the foregoing distillation containing the compound having the structure:

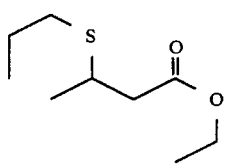

Conditions: Field strength: 100 MHz; Solvent: CFCl₃).

EXAMPLE IV

Preparation of Methyl-4-(Propylthio)Butyrate

Reaction:

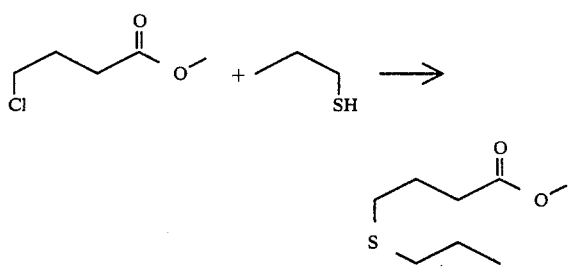

Into a 250 ml reaction flask equipped with reflux condenser, spin bar and hot plate having a built in magnetic stirrer are placed a 25% methanolic solution of sodium methoxide (108 grams; 0.5 moles) and 38 grams (0.5 moles) of n-propyl mercaptan. The resulting mixture is stirred at room temperature for 0.5 hours.

Into a 1 liter reaction flask equipped with electric stirrer, reflux condenser, thermometer, addition funnel and cooling bath are placed 68.2 grams (0.5 moles) of methyl-4-chlorobutyrate having the structure:

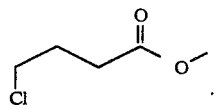

The methyl-4-chlorobutyrate is cooled to 20° C. The mixture of sodium methoxide and n-propyl mercaptan is then poured into the addition funnel. Over a period of 30 minutes while maintaining the pot temperature at 20°–30° C. the premix of n-propyl mercaptan and sodium methoxide is added slowly to the methyl-4-chlorobutyrate reactant. The reaction is exothermic and requires cooling. At the end of the 0.5 hour period, the reaction mass is stirred for a period of 1 hour and the temperature of the reaction mass is permitted to rise to 43° C. The reaction mass is then combined with 500 ml water and transferred to a separatory funnel. The resulting product is then extracted with three 50 ml portions of methylene dichloride. The methylene dichloride extract is then dried over anhydrous sodium sulfate, filtered and distilled on a micro Vigreux column yielding the following fractions:

| Fraction No. | Vapor Temp. (°C.) | Liquid Temp. (°C.) | Vacuum mm/Hg. Pressure |
|---|---|---|---|
| 1 | 91/ | 110/ | 40 |
| 2 | 106 | 128 | 40 |
| 3 | 131 | 134 | 40 |
| 4 | 135 | 136 | 40 |
| 5 | 136 | 137 | 40 |
| 6 | 136 | 137 | 40 |
| 7 | 136 | 137 | 40 |
| 8 | 136 | 137 | 40 |
| 9 | 136 | 137 | 40 |
| 10 | 136 | 145 | 40 |

The resulting product has the structure:

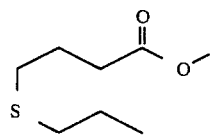

as confirmed by NMR, IR and mass spectral anaylses.

The compound having the structure:

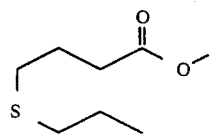

has an excellent green, strawberry, juicy, mushroom and scallion-like aroma and taste profile at 1 ppm causing it to be useful in strawberry, mushroom and gooseberry flavored foodstuffs.

FIG. 8 is the GLC profile for the crude reaction product containing the compound having the structure:

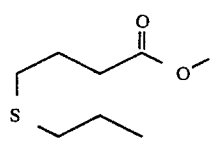

(Conditions: 10′×0.125″ carbowax column programmed at 100°–220° C. at 8° C. per minute). The peak indicated by reference numeral 80 is the peak for the compound having the structure:

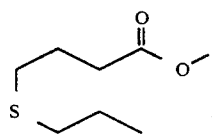

FIG. 9 is the GLC profile for Fraction 6 of the foregoing distillation containing the compound having the structure:

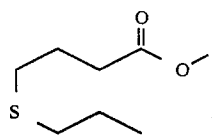

The peak indicated by reference numeral 90 is the peak for the compound having the structure:

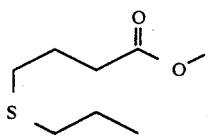

FIG. 10 is the NMR spectrum for Fraction 6 of the foregoing distillation which is the compound having the structure:

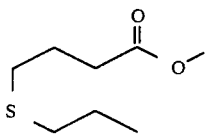

(Conditions: Field strength: 100 MHz; Solvent: CFCl₃).

EXAMPLE V

Preparation of Methyl-4-(Allylthio)Butyrate

Reaction:

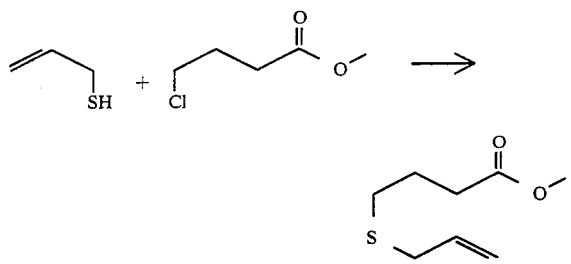

Into a 250 ml reaction flask equipped with magnetic stirrer (built in hot plate) and reflux condenser are placed 108 grams (0.5 moles) of a 25% methanolic solution of sodium methoxide and 37 grams (0.5 moles) of allyl mercaptan. The resulting mixture is stirred for a period of 0.5 hours.

Into a 1 liter flask equipped with cooling bath, thermometer, reflux condenser and addition funnel as well as electric stirrer is placed 68.2 grams of methyl-4-chlorobutyrate. The methyl-4-chlorobutyrate is cooled to 20° C. The mixture of sodium methoxide and allyl mercaptan is added to the addition funnel. Over a period of 0.5 hours while maintaining the pot temperature at 20°–30° C., the mixture of allyl mercaptan and sodium methoxide is added slowly to the methyl-4-chlorobutyrate with stirring. The reaction is exothermic and requires slight cooling. At the end of the addition of the mixture of allyl mercaptan and sodium methoxide, the reaction mass is stirred for 1 hour and the temperature of the reaction mass is permitted to rise to 38° C. 500 ml water are then added to the reaction mass and the reaction mass is transferred to a separatory funnel. The reaction mass is then extracted with three 50 ml portions of methylene dichloride and dried over anhydrous sodium sulfate and filtered. The reaction mass is then distilled on a micro Vigreux column yielding the following fractions:

| Fraction No. | Vapor Temp. (°C.) | Liquid Temp. (°C.) | Vacuum mm/Hg. Pressure |
|---|---|---|---|
| 1 | 75/ | 84/ | 30 |
| 2 | 81 | 91 | 30 |
| 3 | 88 | 99 | 30 |
| 4 | 92 | 108 | 30 |
| 5 | 119 | 125 | 30 |
| 6 | 127 | 128 | 30 |
| 7 | 129 | 130 | 30 |
| 8 | 129 | 130 | 30 |
| 9 | 130 | 133 | 30 |
| 10 | 131 | 136 | 30 |
| 11 | 128 | 150 | 30 |

The resulting product has the structure:

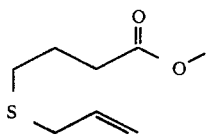

as confirmed by NMR, IR, mass spectral and GLC analyses.

The resulting product has a cashew and Durian aroma and taste profile at 0.01 ppm causing it to be useful in pineapple, cashew, Durian and roasted nut (almond, cashew and hazel nut) flavored foodstuffs.

FIG. 11 is the GLC profile for the crude reaction product containing the compound having the structure:

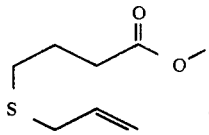

The peak indicated by reference numeral 110 is the peak for the compound having the structure:

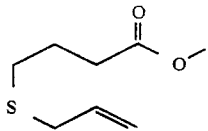

The peak indicated by reference numeral 111 is the peak for the reactant having the structure:

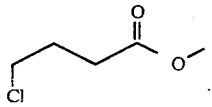

The peak indicated by reference numeral 112 is the peak for the methylene dichloride extraction solvent.

FIG. 12 is the GLC profile for Fraction 10 of the foregoing distillation containing the compound having the structure:

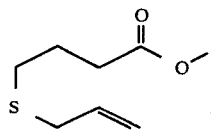

The peak indicated by reference numeral 120 is the peak for the compound having the structure:

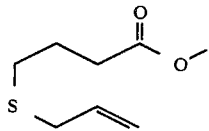

FIG. 13 is the NMR spectrum for the compound having the structure:

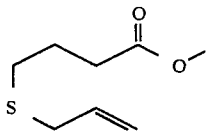

(Fraction 9 of the foregoing distillation) (Conditions: Field strength: 100 MHz; Solvent: CFCl$_3$).

EXAMPLE VI

Preparation of Isobutyl-3-(Propylthio)Butyrate

Reaction:

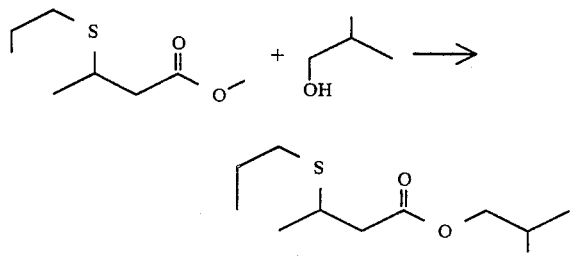

Into a 25 cc micro flask equipped with spin bar, hot plate (equipped with magnetic stirrer), reflux condenser and thermometer are placed 5 grams (0.0284 moles) of methyl-3-(propylthio)butyrate; 8.4 grams (0.1136 moles) of isobutyl alcohol and 0.05 grams of para-toluene sulfonic acid. With stirring, the reaction mass is heated to reflux and refluxed for a period of 14 hours. At the end of the 14 hour period, the reaction mass is cooled and distilled on a micro Vigreux column yielding the following fractions:

| Fraction No. | Vapor Temp. (°C.) | Liquid Temp. (°C.) | Vacuum mm/Hg. Pressure |
|---|---|---|---|
| 1 | 89/ | 98/ | 6 |
| 2 | 93 | 102 | 6 |
| 3 | 94 | 102 | 6 |
| 4 | 85 | 115 | 6 |

The reaction product has the structure:

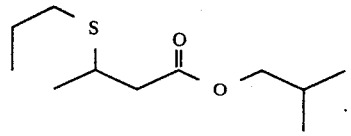

The compound having the structure:

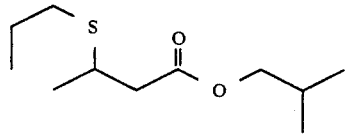

has a green and oniony aroma and taste profile at 2 ppm causing it to be useful in onion flavored foodstuffs.

FIG. 14 is the GLF profile for the crude reaction product containing the compound having the structure:

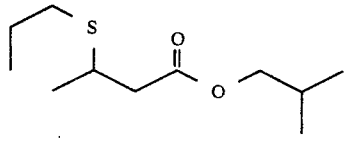

(Conditions: 10'×0.125" SE-30 column). The peak indicated by reference numeral 140 is the peak for the compound having the structure:

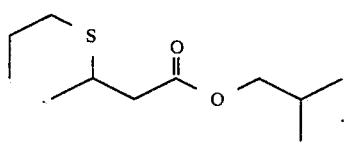

FIG. 15 is the GLC profile for Fraction 4 of the foregoing distillation. The peak indicated by reference numeral 150 is the peak for the compound having the structure:

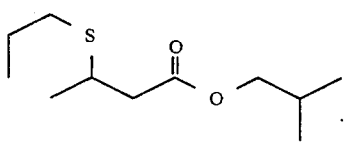

FIG. 16 is the NMR spectrum for Fraction 4 of the foregoing distillation containing the compound having the structure:

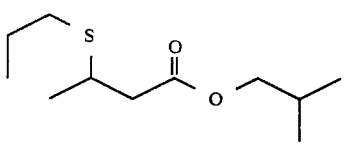

Conditions: Field strength: 100 MHz; Solvent: CFCl$_3$).

EXAMPLE VII

Preparation of Isobutyl-4-(Propylthio) Butyrate

Reaction:

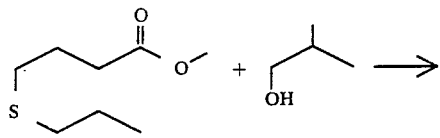

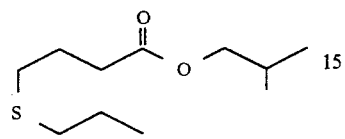

Into a 25 cc micro flask equipped with spin bar, hot plate (having built in magnetic stirrer), reflux condenser and thermometer are placed 5 grams (0.0284 moles) of methyl-4-(propylthio) butyrate; 8.4 grams (0.1136 moles) of isobutanol and 0.05 grams of para-toluene sulfonic acid. The reaction mass is heated to reflux and maintained at reflux with stirring for a period of 14.5 hours. At the end of the refluxing, the reaction mass is cooled and distilled on a micro Vigreux column yielding the following fractions:

| Fraction No. | Vapor Temp. (°C.) | Liquid Temp. (°C.) | Vacuum mm/Hg. Pressure |
|---|---|---|---|
| 1 | 23/ | 25/ | 6 |
| 2 | 84 | 102 | 6 |
| 3 | 103 | 112 | 6 |
| 4 | 105 | 115 | 6 |
| 5 | 95 | 130 | 6 |

The reaction product has the structure:

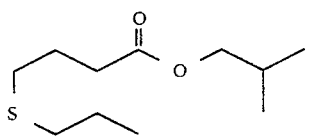

as confirmed by NMR, IR, mass spectral and GLC analyses.

The resulting reaction product has a green, oniony aroma and taste profile causing it to be useful in onion flavored foodstuffs.

FIG. 17 is the GLC profile for the crude reaction product containing the compound having the structure:

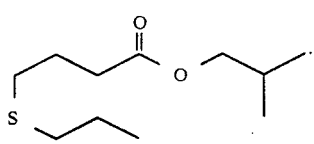

The peak indicated by reference numeral 170 is the peak for the compound having the structure:

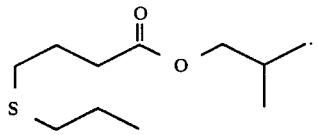

FIG. 18 is the GLC profile for Fraction 5 of the foregoing distillation. The peak indicated by reference numeral 180 is the peak for the compound having the structure:

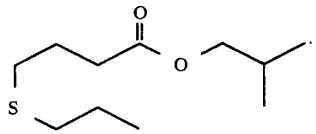

FIG. 19 is the NMR spectrum for Fraction 5 of the foregoing distillation containing the compound having the structure:

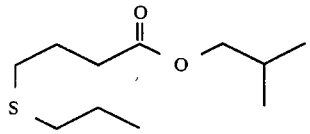

(Conditions: Field strength: 100 MHz; Solvent: CFCl$_3$).

EXAMPLE VIII

Preparation of Isobutyl-4-(Allylthio) Butyrate

Reaction:

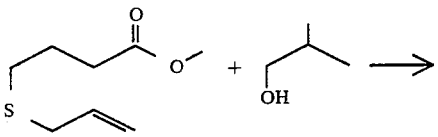

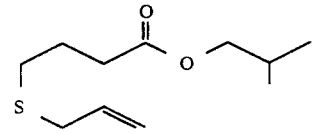

Into a 25 cc micro flask equipped with spin bar, hot plate (having built in magnetic stirrer), thermometer and reflux condenser are placed 5 grams (0.02874 moles) methyl-4-(allylthio) butyrate; 8.5 grams (0.1149 moles) of isobutanol and 0.05 grams of para-toluene sulfonic acid. The reaction mass is heated to reflux and maintained at reflux for a period of 14.33 hours. At the end of the refluxing period, the reaction mass is cooled to room temperature and charged to a distillation flask and distilled on a micro Vigreux column yielding the following fractions:

| Fraction No. | Vapor Temp. (°C.) | Liquid Temp. (°C.) | Vacuum mm/Hg. Pressure |
|---|---|---|---|
| 1 | 24/ | 29/ | 6 |
| 2 | 89 | 104 | 6 |
| 3 | 104 | 113 | 6 |
| 4 | 97 | 120 | 6 |

The resulting product has the structure:

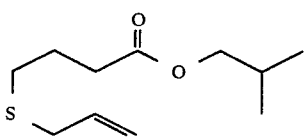

as confirmed by NMR, IR, GLC and mass spectral analyses.

The compound having the structure:

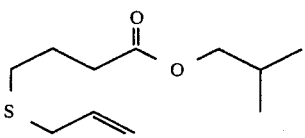

has a green and floral aroma and taste profile at 2 ppm causing it to be useful in Kiwi flavored foodstuffs.

FIG. 20 is the GLC profile for the crude reaction product prior to distillation (Conditions: 10'×125" SE-30 column programmed at 100°–220° C. at 8° C. per minute). The peak indicated by reference numeral 200 is the peak for the compound having the structure:

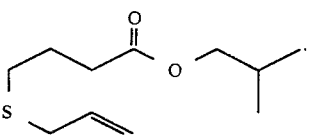

FIG. 21 is the GLC profile for Fraction 4 of the foregoing distillation. The peak indicated by reference numeral 210 is the peak for the compound having the structure:

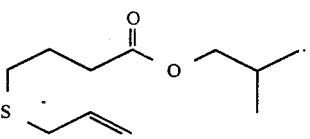

FIG. 22 is the NMR spectrum for Fraction 4 of the foregoing distillation containing the compound having the structure:

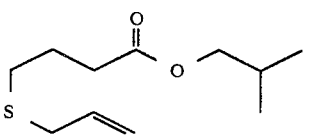

(Conditions: Field strength: 100 MHz; Solvent: CFCl₃).

EXAMPLE IX

Preparation of CIS-3-Hexenyl-3-(Propylthio) Butyrate

Reaction:

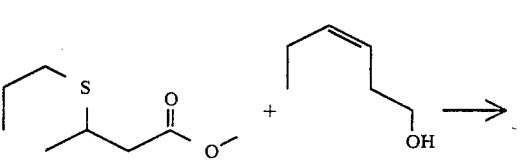

Into a 25 cc micro flask equipped with spin bar, hot plate (having built in magnetic stirrer), reflux condenser and thermometer are placed 5 grams (0.0284 moles) of methyl-3-(propylthio) butyrate; 11.4 grams (0.114 moles) of cis-3-hexenol; and 0.05 grams of para-toluene sulfonic acid. The reaction mass is heated to reflux and refluxed for a period of 14.33 hours. At the end of the refluxing at atmospheric pressure, the reaction mass is cooled and transferred to a distillation flask. The reaction mass is then distilled on a micro Vigreux column yielding the following fractions:

| Fraction No. | Vapor Temp. (°C.) | Liquid Temp. (°C.) | Vacuum mm/Hg. Pressure |
|---|---|---|---|
| 1 | 35/ | 71/ | 6 |
| 2 | 112 | 127 | 6 |
| 3 | 122 | 130 | 6 |
| 4 | 123 | 132 | 6 |
| 5 | 123 | 134 | 6 |
| 6 | 119 | 134 | 6 |

The resulting product has the structure:

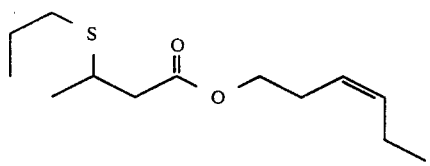

as confirmed by GLC, NMR, IR and mass spectral analyses.

The compound having the structure:

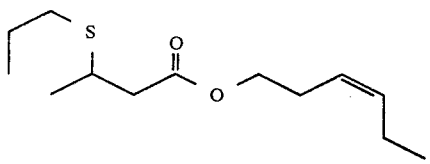

has a roasted onion and garlic aroma and taste profile at 1 ppm causing it to be useful in onion and garlic flavored foodstuffs, including onion soup.

FIG. 23 is the GLC profile for the crude reaction product prior to distillation (Conditions: 10'×0.125" SE-30 column programmed at 100°–220° C. at 8° C. per minute). The peak indicated by reference numeral 230 is the peak for the compound having the structure:

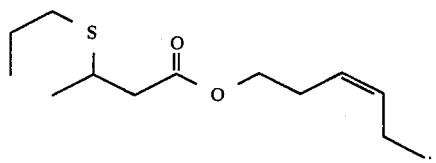

FIG. 24 is the GLC profile for Fraction 5 of the foregoing distillation. The peak indicated by reference numeral 240 is the peak for the compound having the structure:

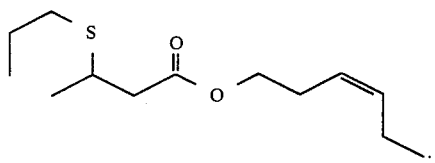

FIG. 25 is the NMR spectrum for Fraction 5 of the foregoing distillation containing the compound having the structure:

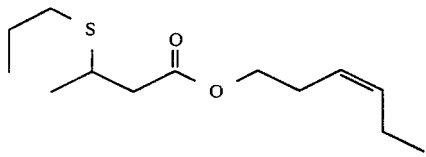

(Conditions: Field strength: 100 MHz; Solvent: CFCl₃).

EXAMPLE X

Preparation of Cis-3-Hexenyl-4-(Propylthio) Butyrate

Reaction:

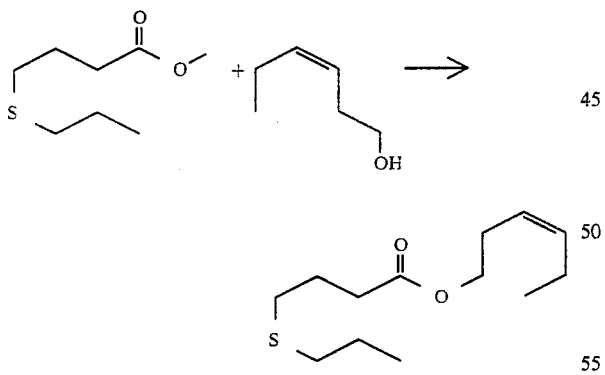

Into a 25 cc micro flask equipped with spin bar, hot plate (having built in magnetic stirrer), reflux condenser and thermometer are placed 5 grams (0.0284 moles) of methyl-4-(propylthio) butyrate; 11.4 grams (0.114 moles) of cis-3-hexenol and 0.05 grams of para-toluene sulfonic acid.

The reaction mass with stirring is heated to reflux and refluxed for a period of 15 hours. At the end of the 15 hour reflux period, the reaction mass is cooled to room temperature and transferred to a distillation flask. The reaction flask is then distilled on a micro Vigreux column yielding the following fractions:

| Fraction No. | Vapor Temp. (°C.) | Liquid Temp. (°C.) | Vacuum mm/Hg. Pressure |
|---|---|---|---|
| 1 | 70/ | 100/ | 6 |
| 2 | 129 | 140 | 6 |
| 3 | 132 | 145 | 6 |
| 4 | 133 | 145 | 6 |
| 5 | 133 | 146 | 6 |

The reaction product has the structure:

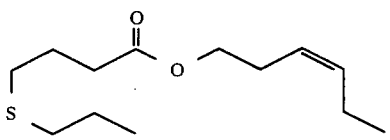

as confirmed by GLC, NMR, IR and pass spectral analyses.

The resulting reaction product has a green, leafy, leek and oniony aroma and taste profile at 5 ppm causing it to be useful in leek-flavored foodstuffs, including leak-flavored cold potato soup.

FIG. 26 is the GLC profile for the crude reaction product (Conditions: 10'×0.125" SE-30 column programmed at 100°-220° C. at 8° C. per minute). The peak indicated by reference numeral 260 is the peak for the compound having the structure;

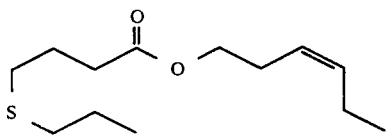

FIG. 27 is the GLC profile for Fraction 4 of the foregoing distillation (Conditions: 10'×0.125" SE-30 column programmed at 100°-220° C. at 8° C. per minute). The peak indicated by reference numeral 270 is the peak for the compound having the structure:

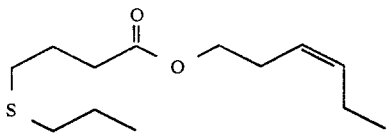

FIG. 28 is the NMR spectrum for Fraction 4 of the foregoing distillation containing the compound having the structure:

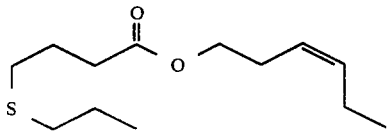

(Conditions: Field strength: 100 MHz; Solvent: CFCl₃).

EXAMPLE XI

Preparation of Cis-3-Hexenyl-4-(Allylthio) Butyrate

Reaction:

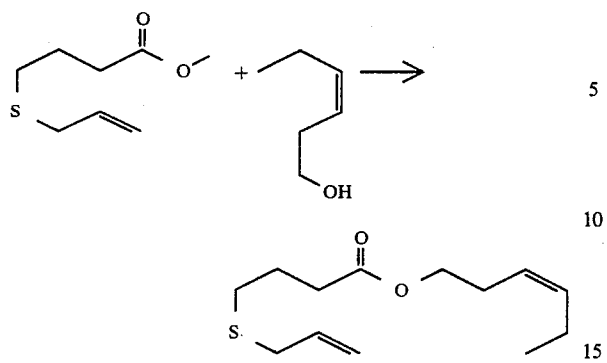

Into a 25 cc micro flask equipped with spin bar, hot plate (having built in magnetic stirrer), reflux condenser and thermometer are placed 5 grams (0.02874 moles) of methyl-4-(allylthio) butyrate; 11.5 grams (0.115 moles) of cis-3-hexenol and 0.05 grams of para-toluene sulfonic acid.

The reaction mass is heated to reflux and refluxed for a period of 14.5 hours. At the end of the 14.5 hour reflux period, the reaction mass is cooled to room temperature and transferred to a distillation flask. The reaction mass is then distilled on a micro Vigreux column yielding the following fractions:

| Fraction No. | Vapor Temp. (°C.) | Liquid Temp. (°C.) | Vacuum mm/Hg. Pressure |
|---|---|---|---|
| 1 | 35/ | 45/ | 6 |
| 2 | 70 | 105 | 6 |
| 3 | 78 | 135 | 6 |
| 4 | 129 | 146 | 6 |
| 5 | 134 | 149 | 6 |
| 6 | 130 | 160 | 6 |

The resulting reaction product has the structure:

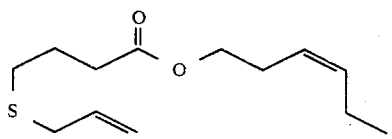

as confirmed by NMR, GLC, IR and mass spectral analyses.

The resulting product has a meaty (mutton-like) aroma and taste profile at 2 ppm causing it to be useful in meat (mutton) and lamb chop flavored foodstuffs.

FIG. 29 is the GLC profile for the crude reaction product containing the compound having the structure:

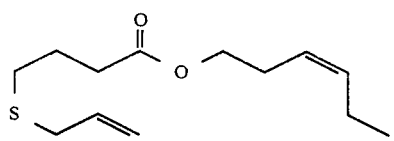

(Conditions: 10' ×0.125" SE-30 column). The peak indicated by reference numeral 290 is the peak for the compound having the structure:

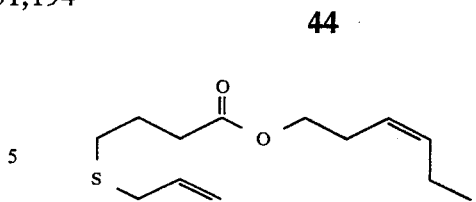

FIG. 30 is the GLC profile for Fraction 5 of the foregoing distillation. The peak indicated by reference numeral 300 is the peak for the compound having the structure:

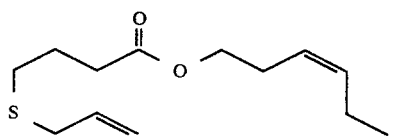

FIG. 31 is the NMR spectrum for Fraction 5 of the foregoing distillation containing the compound having the structure:

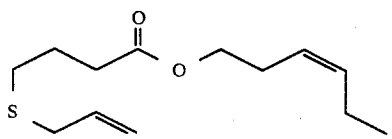

(Conditions: Field strength: 100 MHz; Solvent: CFCl$_3$).

EXAMPLE XII

Preparation of use of the Allyl Ester of 2(3-Hydroxypropylthio) Propionic Acid for Ethyl or Synthetic Meat Flavor The following mixture (A) is prepared:

| Ingredients | Parts by Weight |
|---|---|
| L-cysteine hydrochloride | 1.71 |
| Carbohydrate-free vegetable protein hydrolysate | 28.63 |
| Thiamine hydrochloride | 1.71 |
| Water | 67.95 |

The mixture is refluxed for 4 hours and aged for 3 days to produce reaction product "B".

The following mixture (B) is prepared:

| Ingredients | Parts by Weight |
|---|---|
| Sodium chloride | 30 |
| Monosodium glutamate | 20 |
| Maltodextrin | 30 |
| Levulinic acid | 1 |
| Reaction product "B" | 18 |
| The compound having the structure: 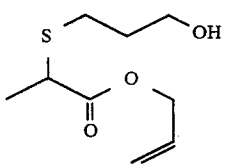 prepared according to Example I. | 1 |

The resulting product has an intense roasted meat flavor, the "roasted" note being augmented by means of the addition of the compound having the structure:

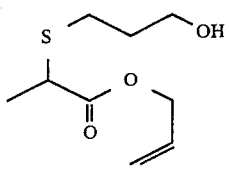

prepared according to Example I. In addition, aesthetically pleasing sesame and bread crust notes are imparted.

EXAMPLE XIII

The following mixture is prepared:

| Ingredients | Parts by Weight |
|---|---|
| Propyl thiopropionate | 10 |
| Compound having the structure: 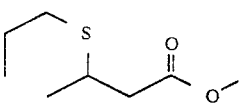 prepared according to Example II. | 10 |
| Natural onion oil | 80 |

The mixture is compared with pure onion oil at the rate of 0.5 ppm in water. The mixture has fuller and fresher aroma and taste characteristics than the natural onion oil alone. The flavor strength of the mixture as compared to the pure natural onion oil is the same.

The foregoing gives rise to the conclusion that the compound having the structure:

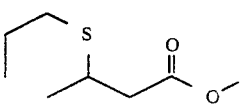

is useful in reconstituting imitation onion oils with onion aroma and taste characteristics. A similar result is obtained when the propylthio propionate is omitted from the foregoing formulation and the compound having the structure:

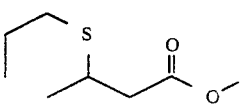

is used alone with the natural onion oil.

EXAMPLE XIV

A 0.9 cc portion of a 0.1 percent solution of the compound having the structure:

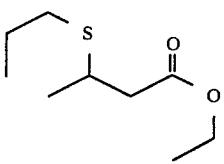

prepared according to Example III in propylene glycol is added to 7.3 grams of a soup base consisting of:

| Ingredients | Quantity |
|---|---|
| Fine ground sodium chloride | 35.62 |
| Hydrolyzed vegetable protein | 27.40 |
| Monosodium glutamate | 17.81 |
| Sucrose | 10.96 |
| Beef fat | 5.48 |
| Sethness caramel color | 2.73 |

The resulting mixture is added to 12 ozs. of a boiling water to create a soup having an excellent onion-garlic-salami flavor, the flavor of garlic and onion being provided by the use of the compound having the structure:

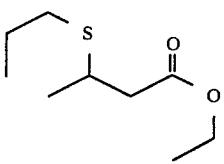

EXAMPLE XV

The compound having the structure:

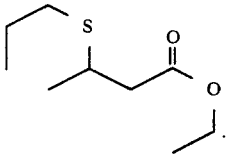

prepared according to Example IV is added to a commercially available mushroom soup at the rate of 1.0 ppm and compared by a bench panel (consisting of 4 individuals) with an unflavored control. The soup flavored with the compound having the structure:

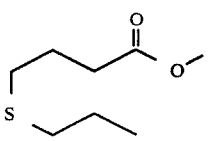

prepared according to Example IV has a stronger mushroom aroma and taste (masking the starch and flour notes present) and is preferred as being more natural and mushroom-like with aesthetically pleasing scallion-like and green nuances.

EXAMPLE XVI

GOYA ® mango nectar (produced by Goya Food Products of Secaucas, N.J.) is admixed at the rate of 0.01 ppm with the compound having the structure:

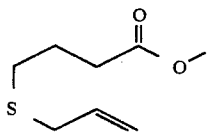

produced according to Example V (in a 25% solution of propylene glycol). The compound having the structure:

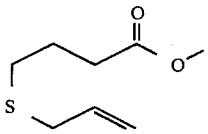

imparts to the mango nectar an interesting cashew and Durian profile causing the mango nectar to be more aesthetically pleasing and more natural-like.

EXAMPLE XVII

The compound having the structure:

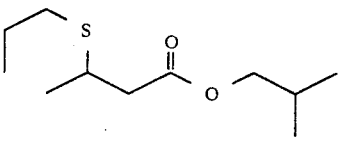

produced according to Example VI is added to a 2% solution of WYLER'S ® "Beef Flavored Instant Bouillon" (manufactured by Wyler Foods, Division of Borden, Inc., Chicago, Ill.) (ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color) at the rate of 5 ppm. The resulting flavor can be described as "beef with onion aroma and taste nuances". The onion taste nuance is enhanced by the addition at the rate of 0.3 ppm of allyl propyl disulfide and allyl propyl trisulfide.

When the compound having the structure:

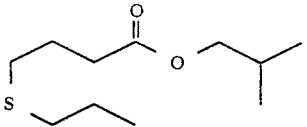

prepared according to Example VII is added to the above-mentioned beef bouillon a similar effect is produced when the compound is added at the level of 7 ppm.

EXAMPLE XVIII

The compound having the structure:

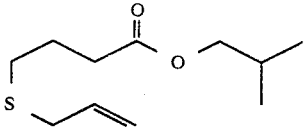

in a 25% solution of propylene glycol is added at the rate of 3 ppm to GOYA ® mango nectar produced by the Goya Food Products of Secaucus, N.J. The mango nectar has imparted thereto an aesthetically pleasing Kiwi aroma and taste nuances which result from the green and floral aroma and taste profile of the compound having the structure:

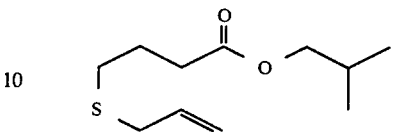

prepared according to Example VIII.

EXAMPLE XIX

The following mixture is prepared:

| Ingredients | Parts by Weight |
|---|---|
| Propyl thioacetate | 20 |
| Propyl thiopropionate | 20 |
| Cyclopentyl thiopropionate | 20 |
| The compound having the structure: 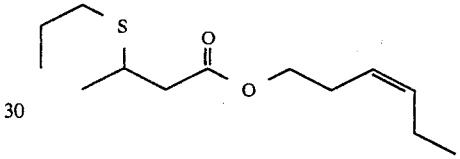 prepared according to Example IX. | 40 |

The above ingredients are thoroughly homogenized at 25° C. The mixture has an excellent roasted onion and garlic flavor. When the resulting mixture is imparted into a meat premix and then cast into a salami, the resulting salami containing 5 ppm of the foregoing flavor formulation has a more intense oniony, garlicy and aged aesthetically pleasing aroma and taste profile.

EXAMPLE XX

A 0.9 cc portion of a 0.1 percent solution of the compound having the structure:

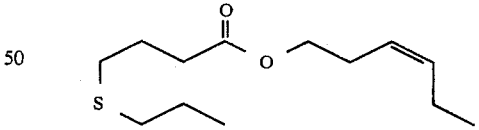

prepared according to Example X in propylene glycol is added to 7.3 grams of a soup base consisting of:

| Ingredients | Quantity |
|---|---|
| Fine ground sodium chloride | 35.62 |
| Hydrolyzed vegetable protein | 27.40 |
| Monosodium glutamate | 17.81 |
| Sucrose | 10.96 |
| Beef fat | 5.48 |
| Sethness caramel color | 2.73 |

The resulting mixture is added to 12 ounces of boiling water to create a soup having an excellent leek and onion flavor.

EXAMPLE XXI

The following ingredients are refluxed for four hours, aged for three days, and spray-dried to produce a solid product having a mutton, "lamb chop" flavor. Before drying, sufficient gum arabic is added to provide a composition containing 0.5 parts gum arabic and one part flavor solids:

| Ingredients | Parts by Weight |
| --- | --- |
| L-Cysteine hydrochloride | 1.32 |
| Carbohydrate-free vegetable protein hydrolysate | 22.05 |
| Compound having the structure: | 1.32 |

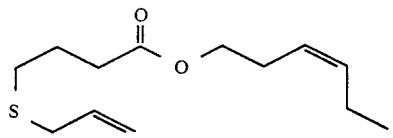

produced according to Example XI.

| Thiamine hydrochloride | 0.50 |
| --- | --- |
| β-Alanine | 1.32 |
| Water | 53.31 |

A similar reaction product without the compound having the structure:

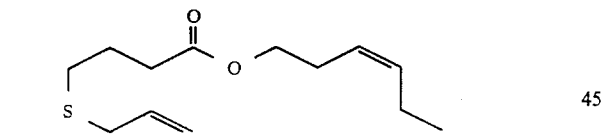

in the reactants does not have the characteristic mutton, "lamb chop" note as does the product with the compound having the structure:

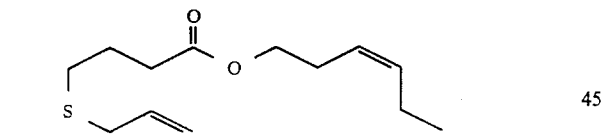

prepared according to Example XI.

What is claimed is:

1. A process for augmenting or enhancing the aroma or taste of a foodstuff comprising the step of adding to said foodstuff from about 0.001 ppm up to about 250 ppm by weight of said foodstuff of an ester of alkylthioalkanoic acid selected from the group consisting of

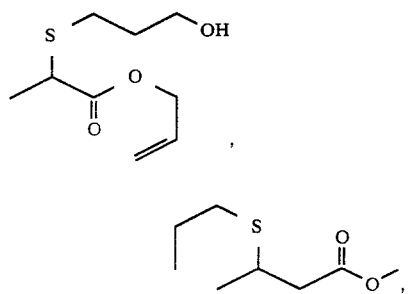

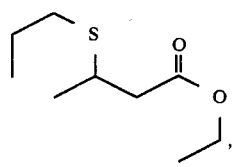

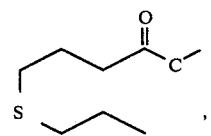

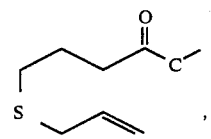

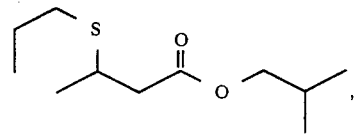

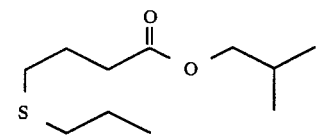

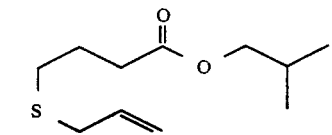

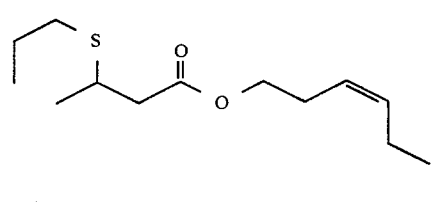

, and

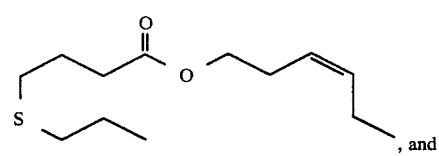

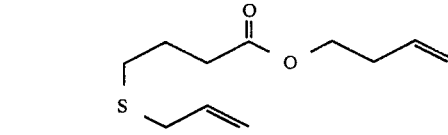

2. The process of claim 1 wherein the ester of alkylthioalkanoic acid has the structure:

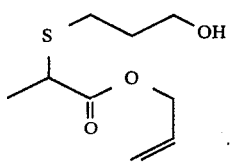

3. The process of claim 1 wherein the ester of alkyl-thioalkanoic acid has the structure:

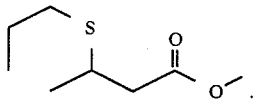

4. The process of claim 1 wherein the ester of alkyl-thioalkanoic acid has the structure:

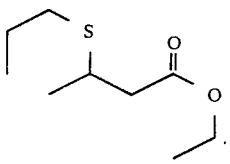

5. The process of claim 1 wherein the ester of alkyl-thioalkanoic acid has the structure:

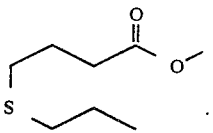

6. The process of claim 1 wherein the ester of alkyl-thioalkanoic acid has the structure:

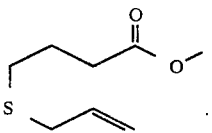

7. The process of claim 1 wherein the ester of alkyl-thioalkanoic acid has the structure:

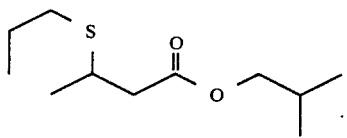

8. The process of claim 1 wherein the ester of alkyl-thioalkanoic acid has the structure:

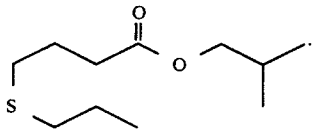

9. The process of claim 1 wherein the ester of alkyl-thioalkanoic acid has the structure:

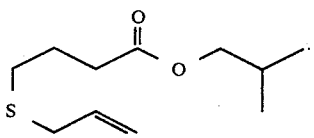

10. The process of claim 1 wherein the ester of alkyl-thioalkanoic acid has the structure:

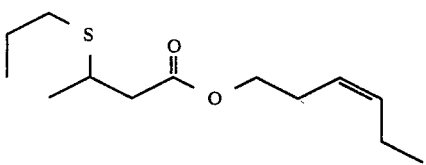

11. The process of claim 1 wherein the ester of alkyl-thioalkanoic acid has the structure:

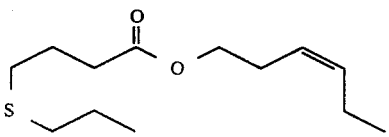

12. The process of claim 1 wherein the ester of alkyl-thioalkanoic acid has the structure:

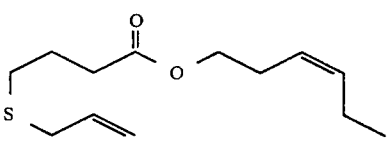

* * * * *